(12) United States Patent
Roth et al.

(10) Patent No.: US 8,889,347 B2
(45) Date of Patent: Nov. 18, 2014

(54) SYSTEMS AND METHODS FOR PERFORMING MEASUREMENTS OF ONE OR MORE MATERIALS

(75) Inventors: Wayne D. Roth, Leander, TX (US);
Charles J. Collins, Austin, TX (US);
Dung Duong, Cedar Park, TX (US);
Edward Calvin, Houston, TX (US)

(73) Assignee: Luminex Corporation, Austin, TX (US)

( * ) Notice: Subject to any disclaimer, the term of this patent is extended or adjusted under 35 U.S.C. 154(b) by 231 days.

(21) Appl. No.: 11/757,841

(22) Filed: Jun. 4, 2007

(65) Prior Publication Data

US 2007/0281311 A1 Dec. 6, 2007

Related U.S. Application Data

(60) Provisional application No. 60/803,781, filed on Jun. 2, 2006.

(51) Int. Cl.
*C12Q 1/68* (2006.01)
*C12M 1/36* (2006.01)
*G01N 21/00* (2006.01)
*G01N 33/543* (2006.01)

(52) U.S. Cl.
CPC .............................. *G01N 33/54333* (2013.01)
USPC .......................... 435/6.1; 435/287.2; 422/68.1

(58) Field of Classification Search
None
See application file for complete search history.

(56) References Cited

U.S. PATENT DOCUMENTS

| | | | |
|---|---|---|---|
| 5,032,381 A | 7/1991 | Bronstein et al. | |
| 5,622,831 A * | 4/1997 | Liberti et al. | 435/7.21 |
| 5,736,330 A | 4/1998 | Fulton | |
| 5,981,180 A | 11/1999 | Chandler et al. | |
| 5,985,153 A * | 11/1999 | Dolan et al. | 210/695 |
| 6,057,107 A | 5/2000 | Fulton | |
| 6,139,800 A * | 10/2000 | Chandler | 422/82.08 |
| 6,165,795 A * | 12/2000 | Mize et al. | 436/69 |
| 6,268,222 B1 | 7/2001 | Chandler et al. | |
| 6,355,491 B1 * | 3/2002 | Zhou et al. | 436/518 |

(Continued)

FOREIGN PATENT DOCUMENTS

| | | |
|---|---|---|
| EP | 0410645 | 1/1991 |
| EP | 1394270 | 3/2004 |

(Continued)

OTHER PUBLICATIONS

Sandin et al., "Magnetophoresis and cytometry with magnetic microparticles," International Congress Series, vol. 1300, 2007, pp. 271-274.

(Continued)

*Primary Examiner* — Betty Forman
(74) *Attorney, Agent, or Firm* — Parker Highlander PLLC

(57) ABSTRACT

Systems and methods for performing measurements of one or more materials are provided. One system is configured to transfer one or more materials to an imaging volume of a measurement device from one or more storage vessels. Another system is configured to image one or more materials in an imaging volume of a measurement device. An additional system is configured to substantially immobilize one or more materials in an imaging volume of a measurement device. A further system is configured to transfer one or more materials to an imaging volume of a measurement device from one or more storage vessels, to image the one or more materials in the imaging volume, to substantially immobilize the one or more materials in the imaging volume, or some combination thereof.

14 Claims, 15 Drawing Sheets

(56) References Cited

U.S. PATENT DOCUMENTS

| | | |
|---|---|---|
| 6,449,562 B1 | 9/2002 | Chandler et al. |
| 6,514,295 B1 | 2/2003 | Chandler et al. |
| 6,524,793 B1 | 2/2003 | Chandler et al. |
| 6,528,165 B2 | 3/2003 | Chandler |
| 6,592,822 B1 | 7/2003 | Chandler |
| 6,649,414 B1 | 11/2003 | Chandler et al. |
| 6,913,877 B1 * | 7/2005 | Chaplen et al. ............... 435/4 |
| 6,939,720 B2 | 9/2005 | Chandler et al. |
| 2002/0051992 A1 * | 5/2002 | Bridgham et al. ............ 435/6 |
| 2003/0040129 A1 * | 2/2003 | Shah ........................... 436/526 |
| 2003/0082587 A1 * | 5/2003 | Seul et al. ..................... 435/6 |
| 2003/0113714 A1 | 6/2003 | Belcher et al. |
| 2003/0170686 A1 * | 9/2003 | Hoet et al. ..................... 435/6 |
| 2003/0186465 A1 | 10/2003 | Kraus et al. |
| 2004/0234898 A1 * | 11/2004 | Batishko et al. ............ 430/312 |
| 2005/0003464 A1 | 1/2005 | Tibbe et al. |
| 2006/0105395 A1 | 5/2006 | Pempsell |
| 2006/0281143 A1 * | 12/2006 | Liu et al. ..................... 435/34 |
| 2007/0064990 A1 | 3/2007 | Roth |

FOREIGN PATENT DOCUMENTS

| | | |
|---|---|---|
| JP | 10-332593 | 12/1998 |
| JP | 2003-114238 | 4/2003 |
| JP | 2005-181145 | 7/2005 |
| WO | 91/09141 | 6/1991 |
| WO | 96/37313 | 11/1996 |
| WO | 97/20214 | 6/1997 |
| WO | 2005/073695 | 8/2005 |
| WO | 2006/079016 | 7/2006 |

OTHER PUBLICATIONS

International Search Report, PCT/US2007/070345, mailed Dec. 14, 2007.

English Translation of Office Communication, issued in Japanese Patent Application No. 2009-513486, mailed on Mar. 27, 2012.

Moser et al., "Microsphere sedimentation arrays for multiplex bioanalytes," *Analytical Chemica Acta*, 558:102-109, 2006.

* cited by examiner

SYSTEMS AND METHODS FOR PERFORMING MEASUREMENTS OF ONE OR MORE MATERIALS

BACKGROUND OF THE INVENTION

1. Field of the Invention

This invention generally relates to systems and methods for performing measurements of one or more materials. In particular, the invention relates to a system and method configured to transfer one or more materials to an imaging volume of a measurement device from one or more storage vessels, to image the one or more materials in the imaging volume, to substantially immobilize the one or more materials in the imaging volume, or some combination thereof.

2. Description of the Related Art

The following descriptions and examples are not admitted to be prior art by virtue of their inclusion within this section.

Instrumentation typically employed in flow cytometry provide viable systems for measuring one or more characteristics of (or "interrogating") internally dyed microspheres (or other particles) to which are coupled fluorescent dyes, fluorophores, or fluorescent tags. The fluorescent dyes, fluorophores, or fluorescent tags coupled to the microspheres may indicate and/or be approximately proportional to a biological reaction that has taken place at the surface of the microspheres. Examples of such instrumentation are described in U.S. Pat. No. 5,981,180 to Chandler et al., which is incorporated by reference as if fully set forth herein. The Luminex 100 line of instruments, which are commercially available from Luminex Corporation, Austin, Tex., essentially are flow cytometers capable of achieving substantially high sensitivity and specificity.

Flow cytometers typically include several relatively sophisticated and expensive devices such as semiconductor lasers, precision syringe pumps, photomultiplier tubes (PMT), and avalanche photo diodes. While performance of such systems is substantially high, the cost of the instruments can be prohibitive for some markets. Additionally, flow cytometers are physically large, heavy and relatively fragile, and typically a trained technician must be on hand at the installation site to perform alignment of the flow cytometers. Flow cytometers also utilize relatively large volumes of sheath fluid to hydrodynamically focus the particle stream into a relatively narrow core.

Imaging using detectors such as charged coupled device (CCD) detectors are employed in several currently available instruments used in biotechnology applications. Many of the commercially available systems are configured to image target human (or other animal) cells. Such systems are not utilized to generate images using different wavelengths of light for determining the identity of the cells or subset to which the cells belong. For multiplexed applications in which CCD detectors are used to measure fluorescent emission of cells, the subset or class of cells or other particles is based on the absolute position of the fluorescence emission within the image rather than the characteristics of the fluorescence emission such as wavelength composition.

Accordingly, it would be desirable to develop systems and methods for performing measurements of one or more materials that are less expensive than currently used systems, that have less complex optical configurations that are more mechanically stable than currently used systems thereby making shipping and installation of the systems easier, that are smaller than currently used systems, that are more sensitive than currently used systems, that have shorter acquisition times and higher throughput than currently used systems, that utilize fewer consumables such as sheath fluid than currently used systems, that enable a final wash of the one or more materials for which the measurements are to be performed, or some combination thereof.

SUMMARY OF THE INVENTION

The problems outlined above are largely addressed by the system and methods of the present invention. The system includes a fluid handling subsystem for loading and removing samples from the device and for cleaning the device or samples. An optics subsystem includes an illumination configuration, such as a plurality of LED's and a collection configuration, such as one or more imaging sensors. Finally, an immobilization subsystem is employed to hold the sample during the measurement interval. In a preferred form, the immobilization subsystem includes a magnet and the sample includes magnetic beads where the magnet can be selectively operated to immobilize the magnetic beads during imaging. In another form, the position of the collection configuration and the illumination configuration in relation to the sample during imaging is optimized.

The following descriptions of various embodiments of systems and methods is not to be construed in any way as limiting the subject matter of the appended claims.

One embodiment relates to a system configured to transfer one or more materials to an imaging volume of a measurement device from one or more storage vessels. This system may be further configured as described herein. Another embodiment relates to a method for transferring one or more materials to an imaging volume of a measurement device from one or more storage vessels. In this method, transferring the one or more materials may be performed as described further herein. In addition, this method may include any other step(s) described herein. Furthermore, this method may be performed by any of the systems described herein.

An additional embodiment relates to a system configured to image one or more materials in an imaging volume of a measurement device. This system may be further configured as described herein. A further embodiment relates to a method for imaging one or more materials in an imaging volume of a measurement device. Imaging the one or more materials may be performed as described further herein. In addition, this method may include any other step(s) described herein. Furthermore, this method may be performed by any of the systems described herein.

Yet another embodiment relates to a system configured to substantially immobilize one or more materials in an imaging volume of a measurement device. This system may be further configured as described herein. Still another embodiment relates to a method for substantially immobilizing one or more materials in an imaging volume of a measurement device. Substantially immobilizing the one or more materials may be performed as described further herein. In addition, this method may include any other step(s) described herein. Furthermore, this method may be performed by any of the systems described herein.

A further embodiment relates to a system configured to transfer one or more materials to an imaging volume of a measurement device from one or more storage vessels, to image the one or more materials in the imaging volume, to substantially immobilize the one or more materials in the imaging volume, or some combination thereof. This system may be further configured as described herein. Another embodiment relates to a method for transferring one or more materials to an imaging volume of a measurement device from one or more storage vessels, imaging the one or more materials in the imaging volume, substantially immobilizing the one or more materials in the imaging volume, or some combination thereof. Transferring, imaging, and substantially immobilizing the one or more materials may be performed as described further herein. In addition, this method may include any other step(s) described herein. Furthermore, this method may be performed by any of the systems described herein.

BRIEF DESCRIPTION OF THE DRAWINGS

Other objects and advantages of the invention will become apparent upon reading the following detailed description and upon reference to the accompanying drawings in which.

Figure 1:
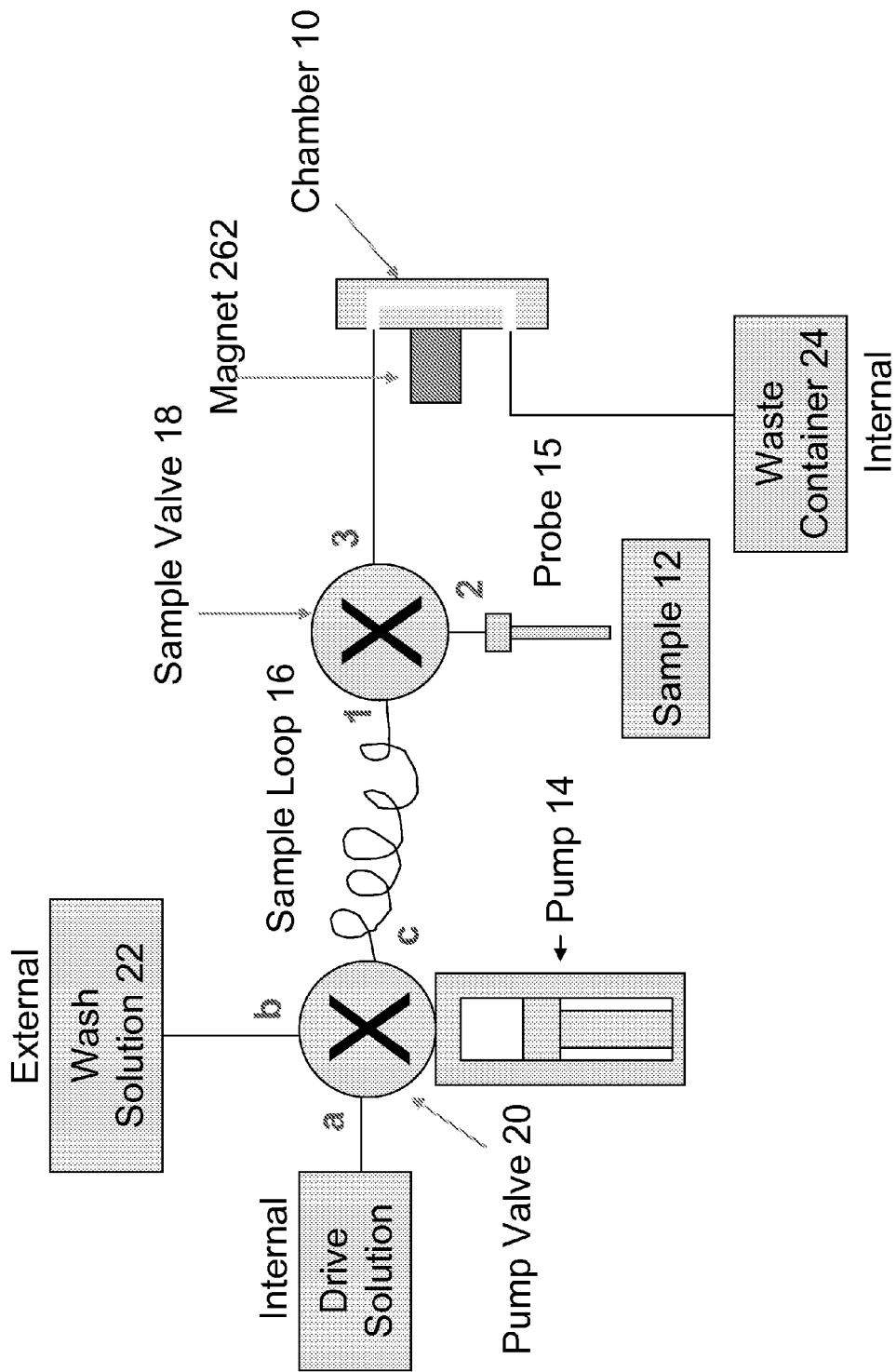
FIG. 1 is a block diagram of the fluid handling subsystem of the present invention.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Although some embodiments are described herein with respect to particles, beads, and microspheres, it is to be understood that all of the systems and methods described herein may be used with particles, microspheres, polystyrene beads, microparticles, gold nanoparticles, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substances known in the art. The particles may serve as vehicles for molecular reactions. Examples of appropriate particles are illustrated in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference as if fully set forth herein. The systems and methods described herein may be used with any of the particles described in these patents. In addition, particles for use in method and system embodiments described herein may be obtained from manufacturers such as Luminex Corporation, Austin, Tex. The terms "particles," "microspheres," and "beads" are used interchangeably herein.

In addition, the types of particles that are compatible with the systems and methods described herein include particles with fluorescent materials attached to, or associated with, the surface of the particles. These types of particles, in which fluorescent dyes or fluorescent particles are coupled directly to the surface of the particles in order to provide the classification fluorescence (i.e., fluorescence emission measured and used for determining an identity of a particle or the subset to which a particle belongs), are illustrated in U.S. Pat. No. 6,268,222 to Chandler et al. and U.S. Pat. No. 6,649,414 to Chandler et al., which are incorporated by reference as if fully set forth herein. The types of particles that can be used in the methods and systems described herein also include particles having one or more fluorochromes or fluorescent dyes incorporated into the core of the particles. Particles that can be used in the methods and systems described herein further include particles that in of themselves will exhibit one or more fluorescent signals upon exposure to one or more appropriate light sources. Furthermore, particles may be manufactured such that upon excitation the particles exhibit multiple fluorescent signals, each of which may be used separately or in combination to determine an identity of the particles.

The embodiments described herein are capable of achieving substantially equivalent or better performance than that of a flow cytometer, while overcoming the issues described in the section above entitled "Description of the Related Art." The embodiments described herein include several configurations using two broad based imaging methods. For fluorescence detection or collection, a single sensor such as a photomultiplier tube (PMT) or avalanche photodiode (APD) per detected wavelength may be employed as commonly used in flow cytometers. However, the particularly preferred embodiments envision a one- or two-dimensional charge coupled device (CCD) or another suitable array detector for fluorescence detection. The excitation source may be configured to provide widespread illumination (i.e., illumination provided over a relatively large area of the imaging volume of the measurement device (such as the entire imaging volume of the measurement device) simultaneously) using light emitted by light sources such as light emitting diodes (LEDs) and delivered to one or more materials in the imaging volume of the measurement device directly or via fiber optics. Alternatively, the excitation source may be configured to provide illumination of a relatively small spot in the imaging volume of the measurement device, and the system may be configured to scan the relatively small spot across the imaging volume. In this manner, the illumination may be configured as a relatively "tiny flying spot" of focused light generated from one or more LED's, one or more lasers, one or more other suitable light sources, or some combination thereof.

The embodiments described herein also provide a number of advantages over other systems and methods for performing measurements of one or more materials. For example, the embodiments described herein are advantageously less expensive than other systems and methods. In particular, in several configurations described herein, the embodiments may include a relatively inexpensive CCD as a photon detector rather than a PMT, relatively simple LED's in place of lasers, a relatively inexpensive pump in place of a precision syringe pump to move fluids, or some combination thereof. Thus, the aggregate cost of the embodiments described herein can be reduced by approximately an order of magnitude. In addition, the embodiments described herein are advantageous due to a substantially simpler optical configuration than that typically used for flow cytometry thereby rendering the embodiments described herein substantially mechanically stable. Such mechanical stability enables shipping the system embodiments described herein via a standard shipping service (e.g., a UPS-type service). Furthermore, such mechanical stability allows the system embodiments described herein to be installed by a user who may or may not be a technically adept service person. Moreover, the embodiments described herein are advantageous since the system embodiments can be substantially small (e.g., conceivably the size of a pocket camera).

Another advantage of the embodiments described herein is that the embodiments provide the ability to integrate photons over a time period much longer than a few microseconds as is typical using a laser-based flow cytometer type system. Therefore, the embodiments described herein are capable of detecting particles with fewer molecules of fluorescence on the surface or otherwise coupled thereto than currently used systems and methods. As such, the embodiments described herein may advantageously have a higher sensitivity than other currently used systems and methods. In addition, the embodiments described herein may have substantially shorter measurement acquisition times and therefore higher throughput than currently used systems. For example, in embodiments configured to use a CCD/LED "flood-illumination" configuration, acquisition of sample measurements is faster since an entire sample or an entire population of particles can be measured in two or three images or "pictures," rather than serially particle by particle. In another example, for users that desire a relatively high throughput solution, a CCD/LED based system provides a comparatively inexpensive system, and in several instances, can be operated in parallel to quickly process a single microtiter plate or other sample.

Yet another advantage of the embodiments described herein is that sheath fluid is not used to hydrodynamically focus the particles as in flow cytometry. Still another advantage of the embodiments described herein is that a final "wash" of the one or more materials for which measurements are to be performed is possible within the system to remove free fluorochromes or other materials that will interfere with the measurements from the liquid surrounding the particles thereby lowering the background light detected by the measurement device (e.g., by the imaging sensors of the measurement device).

The description of the embodiments provided further herein is generally divided into three subsections, in which different system embodiments are described. For example, one subsection relates to fluidic configurations that may be included in the system embodiments described herein. The fluid handling configurations can be used to introduce or transfer the one or more materials (e.g., beads and other reagents or beads after one or more reactions have been allowed to take place on the surface of the beads) to an imaging volume of the measurement device from one or more storage vessels. Another subsection relates to optical configurations that may be included in the system embodiments described herein. In general, the different optical configurations include different combinations of excitation sources and photon detectors, sometimes known herein as illumination modules and collection modules. An additional subsection relates to particle immobilization configurations and methods that may be included in, or used by, the system embodiments described herein. The systems described herein may include such particle immobilization configurations since in an imaging system, the particles preferably do not move substantially during the measurement interval. Note that any combination of the system configurations described in the three subsections above may be combined to produce a final imaging system embodiment.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

First Preferred Embodiment

Figure 2:
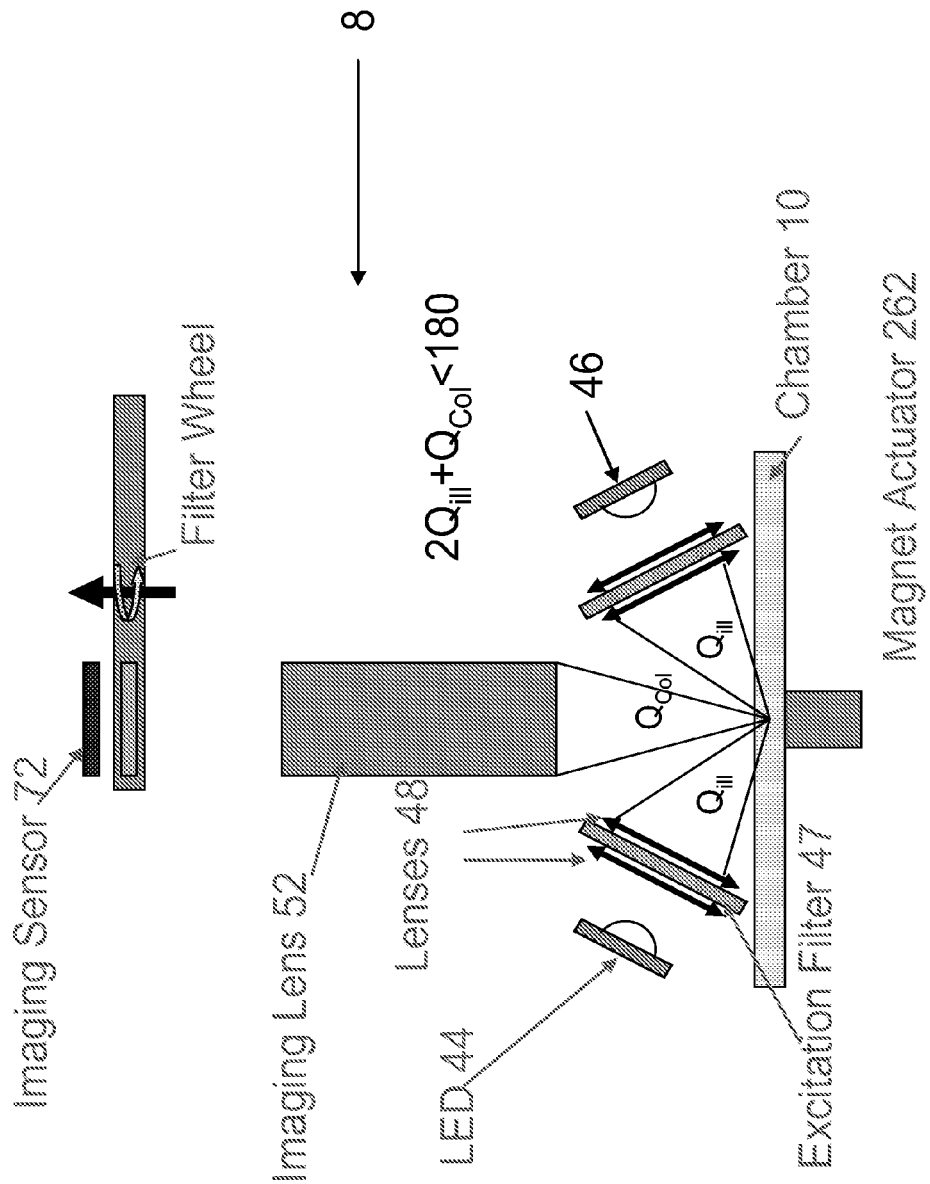
FIG. 2 is a block diagram depicting the optical configuration of a device of the present invention.

FIGS. 1-4 are illustrative of the first embodiment. This embodiment relates generally to a system configured to transfer one or more materials to an imaging volume of a measurement device from one or more storage vessels. As noted above, the system has three major components: fluid handling 6, optic configuration 8, and particle immobilization subsystem (not shown in FIG. 1). FIG. 1 shows the functional components of the fluid handling subsystem while FIG. 2 illustrates the functional components of the optics subsystem.

In the fluid handling subsystem of FIG. 1, samples are transferred into imaging volume 10 of the measurement device from sample storage vessel 12. The imaging volume may be configured as an imaging chamber 10, which may have any suitable configuration known in the art. Storage vessel 12 may be configured as a micro titer plate or any other suitable sample container known in the art.

The system also includes a bi-directional pump 14 configured to draw fluid into a storage reservoir and to later expel fluid from the storage reservoir into the imaging volume of chamber 10. Pump 14 may have any suitable configuration known in the art. Since the particles are substantially immobilized during the exposure time as described further herein, pulse-free flow such as that obtained from an expensive syringe pump is not required for the system embodiments described herein. A sufficient reservoir can be formed out of a length of tubing 16 between pump 14 and sample valve 18. Such a reservoir is commonly called a "sample loop." The tubing may have any suitable configuration. The function of sample valve 18 is to connect a sample probe 15 to the reservoir (sample loop 16) when aspirating from storage vessel 12 (e.g., the micro titer plate) and to connect the reservoir to the imaging chamber 10 when dispensing. Sample valve 18 may include any suitable valve known in the art.

Wash valve 20 is utilized at the pump end of the storage reservoir to allow fresh water (or other suitable reagent) from storage vessel 22 to flow to the imaging volume of imaging chamber 10. Wash valve 20 may include any suitable valve known in the art. In alternative embodiments, the sample and wash valves could be combined into a single valve (not shown). Pump 14 may also be configured to transfer the one or more materials and any other fluid in imaging volume 10 to waste vessel 24. Waste vessel 24 may have any suitable configuration known in the art.

There are two primary modes of operating the fluid handling subsystem 6 to load a sample in the imaging chamber 10, namely a load procedure with sample wash and a load procedure without sample wash. Referring to FIGS. 1 and 2, the load procedure with NO sample wash generally occurs as follows:

Clean System
1) Pump Valve 20 to position a.
2) Load Drive Solution.
3) Pump Valve 20 to position c.
4) Sample Valve 18, mover from position 1 to 3.
5) Move magnet 262 back (away from imaging chamber 10).
6) Push Drive Solution through chamber to clean chamber 10.
7) Sample Valve 18, position 1 to 2.
8) Push Drive solution through Probe 15 to clean Probe.

Load Sample
1) Pump Valve 20 to position a.
2) Load Drive Solution.
3) Pump Valve 20 to position c.
4) Sample Valve 18, position 1 to 2.
5) Lower probe 15 into sample well 12.
6) Load a sample into sample loop 16.
7) Raise probe 15 and pull until air is at sample valve 18 and entire sample is in sample loop 16.
8) Sample Valve 18, position 1 to 3.
9) Move magnet 262 forward (toward imaging chamber 10).
10) Push Sample from sample loop 16 into imaging chamber 10 capturing magnetic beads.
11) Take Images with the sample immobilized.

Clean System
1) Pump Valve 20 to position a.
2) Load Drive Solution.
3) Pump Valve 20 to position c.
4) Sample Valve 18, position 1 to 3.
5) Move magnet 262 back (away from imaging chamber 10).
6) Push Drive Solution through chamber 10 to clean chamber.
7) Sample Valve 18, position 1 to 2.
8) Push Drive solution through Probe 15 to clean Probe.

The load procedure with sample wash generally occurs as follows:

Clean System
1) Pump Valve 20 to position a.
2) Load Drive Solution.
3) Pump Valve 20 to position c.
4) Sample Valve 1 to 3.
5) Move magnet 262 back (away from chamber 10).
6) Push Drive Solution through chamber 10 to clean chamber.
7) Sample Valve 18, position 1 to 2.
8) Push Drive solution through Probe 15 to clean Probe.

Preload Wash Solution
1) Pump Valve 20 to position b.
2) Load Wash Solution.
3) Pump Valve 20 to position c.
4) Sample Valve 1 to 3.
5) Push Wash Solution through chamber.
6) Sample Valve 18, position 1 to 2.
7) Push Wash solution through Probe 15(*sample* loop 16 and probe 15 preloaded with Wash Solution).

Load Sample
1) Pump Valve 20 to position a.
2) Load Drive Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 forward (toward chamber 10).
10) Push Sample from sample loop 16 into chamber 10 capturing magnetic beads.
11) Push Wash Solution in sample loop 16 behind sample over captured magnetic beads to "Wash" beads.
12) Take Images with the sample immobilized.

Clean System
1) Pump Valve 20 to position a.
2) Load Drive Solution.
3) Pump Valve 20 to position c.
4) Sample Valve 18, position 1 to 3.
5) Move magnet 262 back (away from chamber 10).
6) Push Drive Solution through chamber 10 to clean chamber.
7) Sample Valve 18, position 1 to 2.
8) Push Drive solution through Probe 15 to clean Probe.

An advantage of using the second loading procedure where the sample is "washed" is to remove from the surrounding solution fluorochromes that are not bound to the surface of a bead. For the convenience of processing, some assays do not perform this final wash step, resulting in excitation of the extraneous fluorophores, which results in a "background" signal when the assay response from beads is measured. Thus, these no-wash assays have a poorer limit of detection than washed assays.

Unlike a flow cytometer, the system of the present invention inherently provides the ability to dispense with the fluid surrounding the beads, thereby washing away the free fluorochromes. This is possible because the beads are magnetically attached to the substrate (when the magnet is brought into contact with the back of the chamber), and will not move if a new "fresh" fluid is injected into the chamber, thereby displacing the fluorochrome laden liquid.

Figure 8:
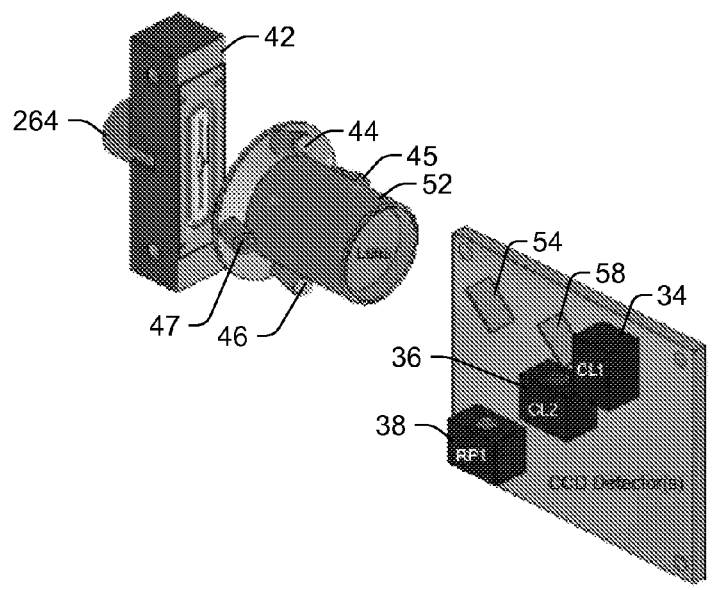
FIG. 8 is a schematic diagram illustrating an isometric side view of one embodiment of a system configured to image one or more materials in an imaging volume of a measurement device.
Figure 21:
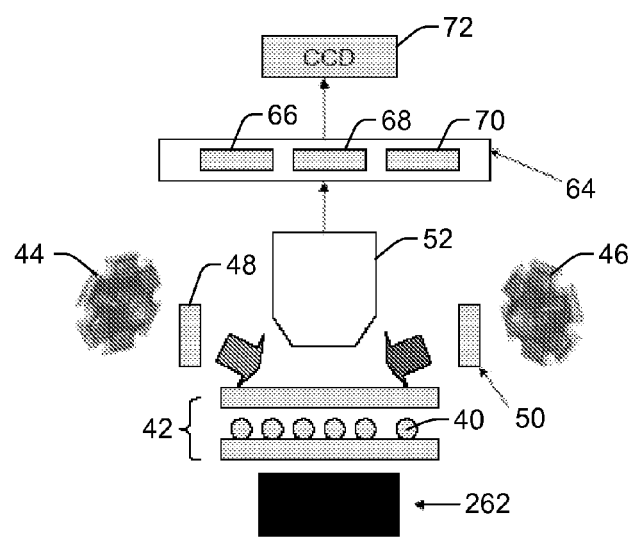
FIG. 21 is a schematic diagram illustrating a side view of another embodiment of a system configured to image one or more materials in an imaging volume of a measurement device and to substantially immobilize the one or more materials in the imaging volume.

Turning to FIG. 2, the optics subsystem 8 is broadly illustrated. This subsystem 8 includes magnetic element 262 positioned on the side of imaging chamber 10 opposite the optics of the system. Magnetic element 262 may include any suitable magnetic element known in the art such as a permanent magnet or an electromagnet that can be used to generate a suitable magnetic field. In this manner, dyed particles, e.g. beads, with embedded magnetite may be used such that the particles can be substantially immobilized in imaging chamber 10 (e.g., at the bottom of the chamber) using a magnetic field generated by magnetic element 262 at the side of the chamber. Although magnetic element 262 is shown adjacent to imaging chamber 10 in FIG. 2, (see also FIG. 8 where magnetic element 264 is in contact with (or coupled to) imaging chamber 10 on the side of the imaging chamber opposite the optical elements of the system) the magnetic element may be selectively spaced from the imaging chamber 10 as shown in FIG. 21. Magnetic element 262 may be further configured as described above. In addition, although FIGS. 2, 8 and 21 show one magnetic element positioned proximate the imaging chamber, it is to be understood that the system may include more than one magnetic element, each of which is positioned proximate the side of the imaging chamber opposite the optics of the system.

After signal acquisition by the measurement device, the magnetic field may be removed (e.g., by using a solenoid to move a permanent magnet or by turning an electromagnet on and off with a switch), and the particles may exit the imaging chamber 42, while new particles from the next sample are brought into the chamber 42. The particles in the imaging chamber 10 may be removed and particles may be introduced to the imaging chamber using any of the embodiments described herein. The system shown in FIG. 2 may be further configured as described herein.

The simplest imaging chamber 10 design is an imaging chamber that has a relatively smooth internal surface on the side of the imaging chamber proximate the magnetic element such that the beads are randomly distributed across this internal surface as the magnet 262 pulls them down. However, the imaging chamber 10 can also be designed to "hold" the beads in particular spots when the magnetic field is applied as described in more detail herein.

Figure 3:
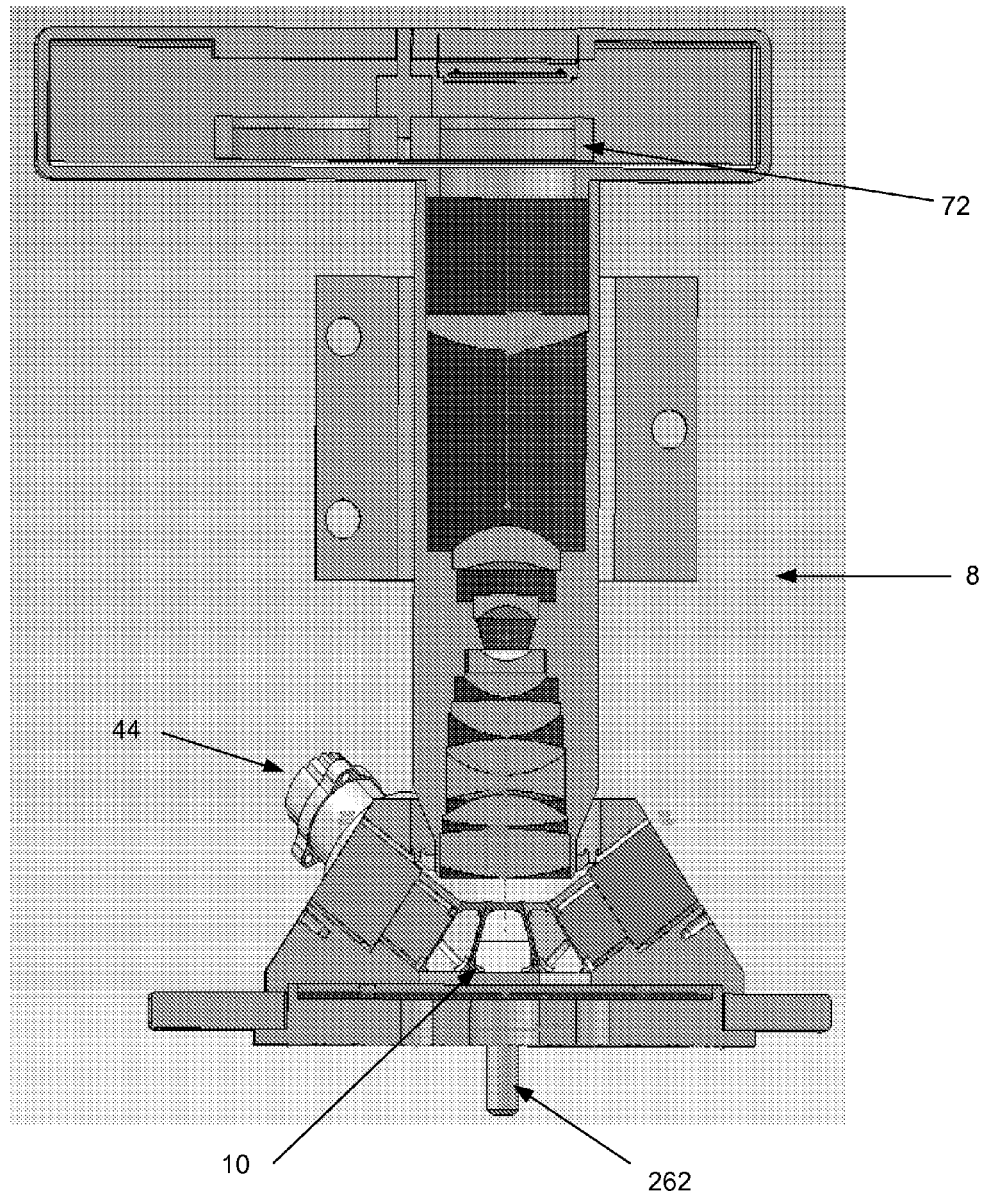
FIG. 3 is vertical cross section with parts broken away of a device of the present invention showing one version of the block diagram of FIG. 2.
Figure 4:
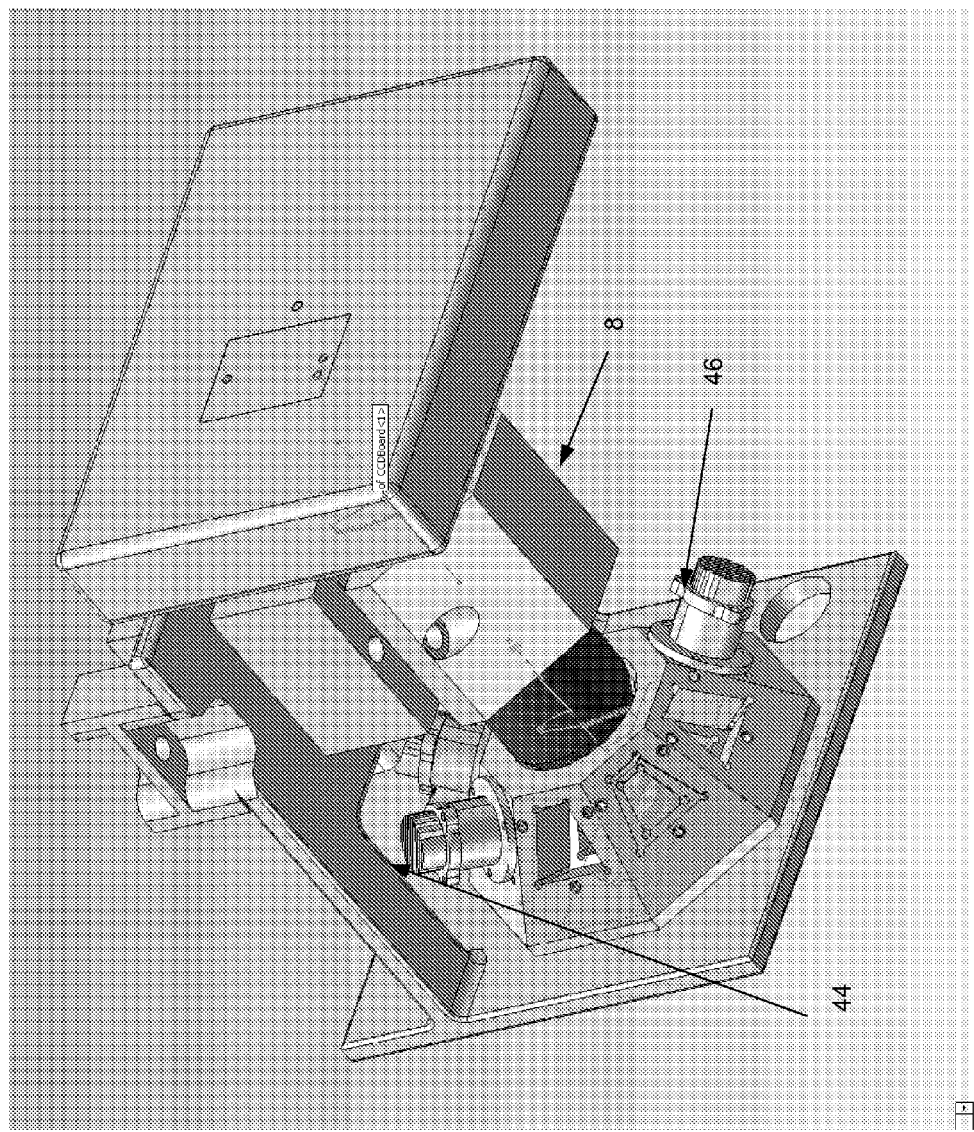
FIG. 4 is a perspective view of the device of FIG. 3.

FIGS. 3 and 4 are depictions of what a measurement device in accordance with the present invention might look like incorporating the functional components described in FIGS. 1 and 2.

Broadly speaking, the method of operating the measurement device of FIGS. 1-4 involves exposing the analytes of interest to a bead population to create a sample, which is stored in a sample vessel 12 as shown in FIG. 1. The sample is loaded into an imaging chamber 10, using, e.g. the sample handing steps described above. The sample is immobilized in the imaging chamber 10 by the selective operation of the magnet 262. Optionally, the immobilized sample can be washed to remove extraneous fluorospheres. With the sample immobilized in the chamber 10, the illumination module (LED's 44, 46) is operated to excite the sample. The imaging sensor 72 (CCD) captures the image and the image is processed (See, e.g. U.S. Patent Application Ser. No. 60/719,010 entitled "Methods and Systems for Image Data Processing" filed Sep. 21, 2005 by Roth, which is incorporated by reference as if fully set forth herein.) The magnet 262 releases the sample and the device is cleaned.

Figure 26:
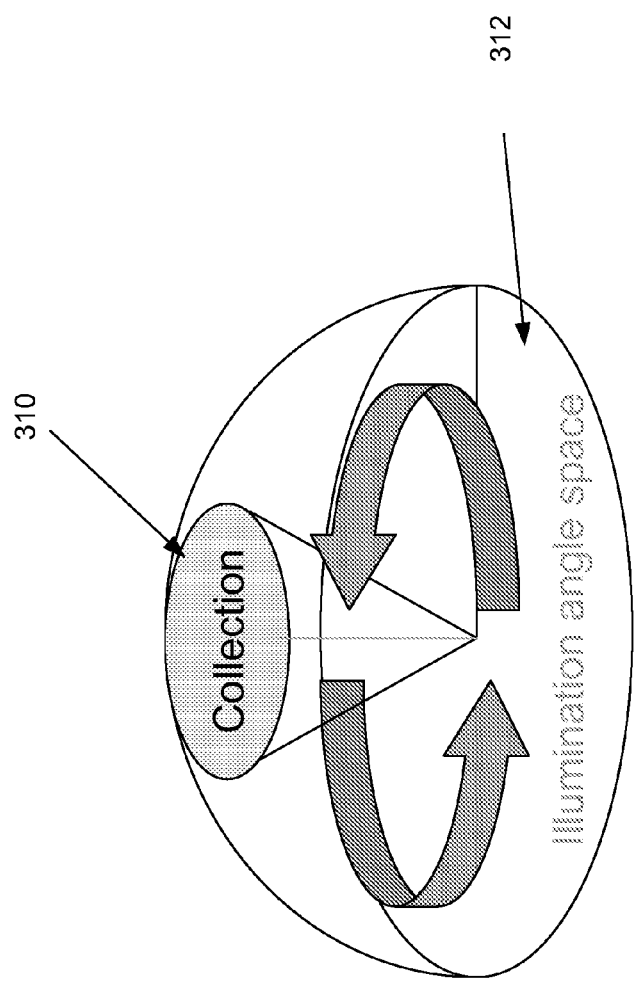
FIG. 26 is a schematic illustrating the collection and illumination angle space.

It is believed that the position of the imaging sensors 72 in relation to the LED's 44, 46, chamber 10 and magnet 262 can be optimized for imaging beads in accordance with the present invention. Beads have distinct characteristics, namely the dye within the beads and reporter molecules on the beads, both absorb and re-emit photons in no preferred direction (uniformly over all angles). The positions of the illumination by the LED's 44, 46 and imaging sensors (CCD 72) is chosen to optimize the "angle space" of any beads in the Field of View (FOV) of the imaging sensors (any beads that can be seen by the CCD 72). Since the magnet 262 is on the back of the chamber 10, the angle space available for the illumination and imaging systems is a hemisphere above the magnet. This is illustrated in FIG. 26 where "collection" 310 is the solid angle collected by the imaging sensors 72 and "illumination angle space" 312 is the space that the illumination modules can occupy. The more coverage over this illumination angle space 312 by the illumination optics (LED's 44, 46 in FIG. 2), the more power imparted on the beads during imaging. Similarly, the higher the collection angle (Numerical Aperture) over the illumination angle space 312, the more flux the imaging lens 52 (FIG. 2) can collect and deliver to the imaging sensor 72 (CCD detector). A balance must be made between the angles allocated for the imaging sensors and the illumination system.

For low-cost manufacturability, the imaging lens 52 practical limit for numerical aperture is around 0.3 for a magnification of 4. For higher magnifications, the numerical aperture of imaging lens 52 could increase while maintaining the same cost guidelines. Other factors that effect the cost of the lens 52 are Field of View and broadness of waveband. A numerical aperture of 0.3 is roughly 35 degrees full angle.

For the positioning of the illumination module, e.g. the LED's 44, 46, the limit may be the LED's brightness as well as the cost of the excitation filters 47. The etendue of the LED will dictate what of the bead's angle space is needed to provide the maximum LED flux over the field of view (FOV). (Etendue is the Area of the source multiplied by the solid angle of the source: it defines the geometry characteristics of the emitted flux.) If the FOV is relatively large, the angle space required will be lower and therefore more LED's can be used. However, more LED's will add cost to the system. Again, a balance between costs vs. performance must be determined.

Figure 27:
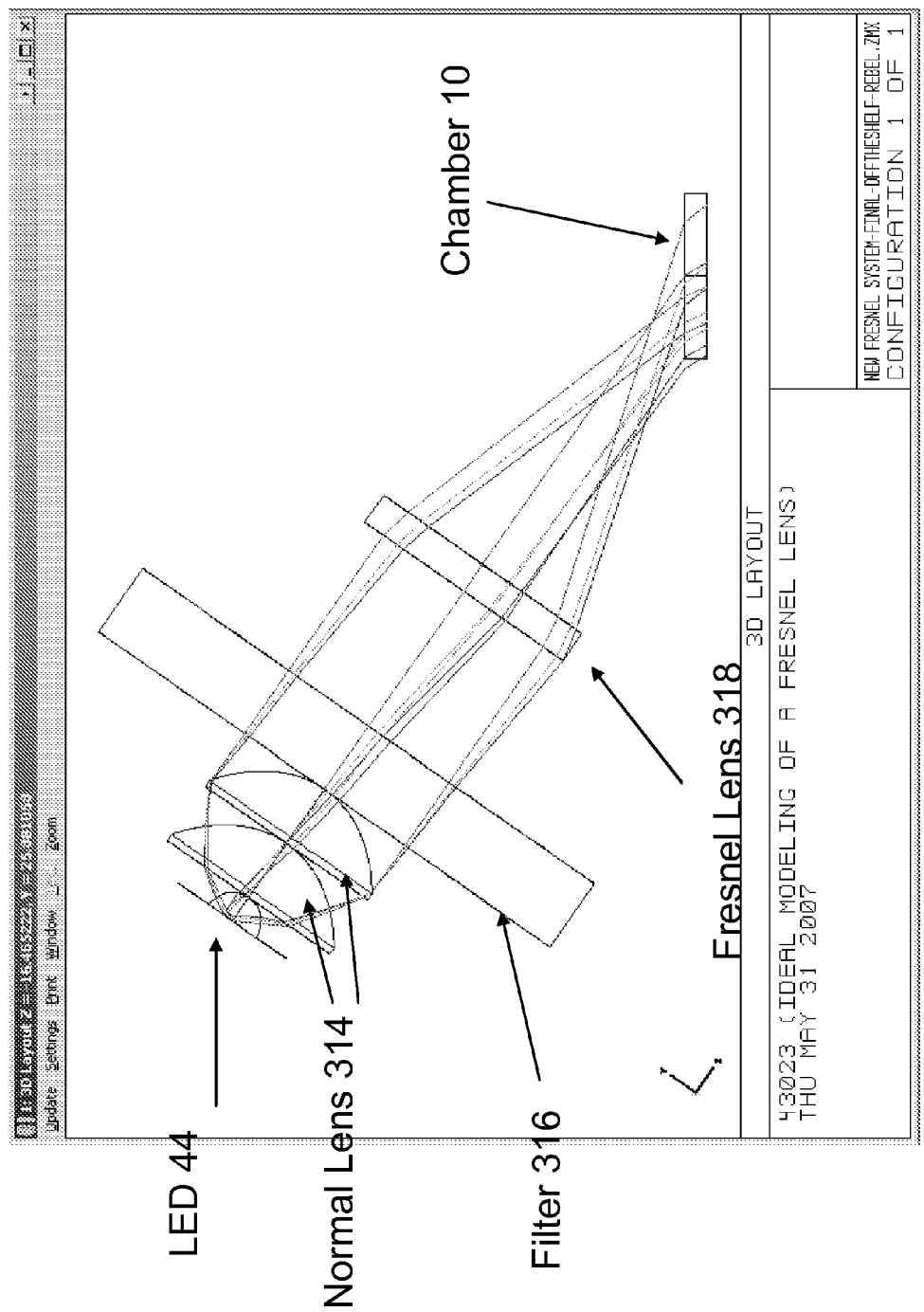
FIG. 27 is vertical profile view of an illumination module in accordance with a preferred embodiment of the device of the present invention.

Comparing FIGS. 2 and 27, the first embodiment includes an illumination module consisting of lens, filters, and one or more LED's 44/46, as shown in FIG. 27. As shown in FIG. 27, associated with each LED 44 is a lens system comprising two normal refractive lenses 314. The lenses 314 are used to collect as much light from the LED 44 as possible and pseudo-collimate it through the filter 316. Though one normal refractive lens 314 can be used, the collected angle is much less, thus leading to an inefficient illumination system and a preference for two or more lenses 314.

Normal refractive lens 314 are used prior to the filter 316 because there is inherently scatter at the edges of the fresnel lens grooves. Scattered light can pass through the filter 316 at non-optimal angles and increase the out-of-band background at the image. This would lead to increased background noise. The fresnel lens 318 is used after the filter 316 to re-focus the light onto the chamber 10. Some blurring may be necessary to ensure uniformity at the image plane. The fresnel lens 318 is used because of cost as well as physical extent. The fresnel lens 318 is relatively thin. The primary cost component in the illumination module of FIG. 27 is the excitation filter 316. The molded plastic refractive lenses 314 as well as the fresnel lens 318 are low cost. The LED 44 is also inexpensive.

Conservation of brightness dictates that the etendue must be preserved in an optical system to maximize efficiency. The etendue (in air)=$A\omega$, where A is the area and $\omega$ is the solid angle. The ramification is that the image size along with the imaging optics magnification dictates the field of view of the illumination module of FIG. 27. Using the brightness equation, the angle space needed for the illumination module can be calculated from the FOV of the optics. This angle space allows for the determination of the minimum number of LED's necessary to provide the maximum flux (power) to the FOV. More LED's will not increase the power to the FOV. Optimizing the angle space utilized by the illumination and imaging systems can be accomplished by applying the brightness equation. However, in the system of FIGS. 2-4, other tradeoffs must also be made such as cost and performance.

The first embodiment depicted in FIGS. 2-4 is configured to substantially immobilize the beads in an imaging volume of chamber 10 is shown in FIG. 2. Magnetic element 262 is positioned on the side of imaging chamber 10 opposite the optics of the system (illumination and collection modules). Magnetic element 262 may include any suitable magnetic element known in the art such as a permanent magnet or an electromagnet that can be used to generate a suitable magnetic field. In this manner, dyed beads with embedded magnetite may be used such that the beads can be substantially immobilized in imaging chamber 10 (e.g., at the bottom of the chamber) using a magnetic field generated by magnetic element 262 at the back side of the chamber. Although magnetic element 262 is shown adjacent the imaging chamber 10 in FIG. 2, magnetic element 262 may be in contact with (or coupled to) or spaced from imaging chamber 10 on the side of the imaging chamber opposite the optical elements of the system.

After signal acquisition by the measurement device, the magnetic field may be removed (e.g., by using a solenoid to move a permanent magnet or by turning an electromagnet on and off with a switch), and the beads may exit the imaging chamber 10, while new beads from the next sample are brought into the chamber 10. The beads in the imaging chamber 10 may be removed and beads may be introduced to the imaging chamber 10 using any of the embodiments described herein.

The design of the imaging chamber 10 in FIG. 2 is a relatively smooth internal surface on the side of the imaging chamber 10 proximate the magnetic element 262 such that the beads are randomly distributed across this internal surface as the magnet pulls them down. However, the imaging chamber 10 can also be designed to "hold" the beads in particular spots when the magnetic field is applied as described in additional embodiments herein.

Additional Embodiments

Figure 5:
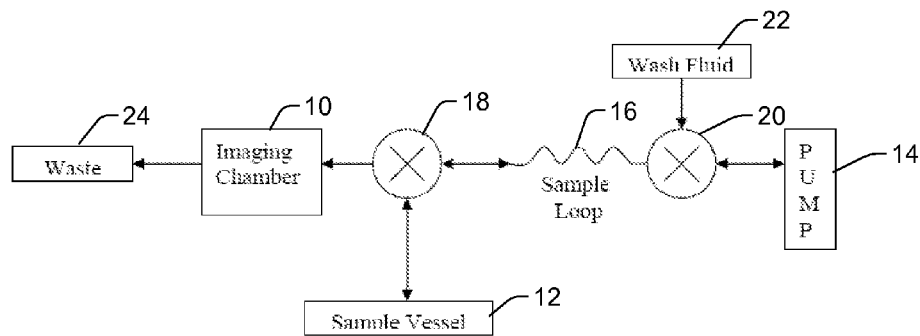
FIGS. 5-7 are schematic diagrams illustrating block diagrams of various embodiments of a system configured to transfer one or more materials to an image volume of a measurement device from one or more storage vessels.

Another embodiment of such a system in accordance with the present invention is shown in FIG. 5. In this embodiment, samples are transferred into imaging volume 10 of the measurement device (not shown in FIG. 5) from storage vessel 12. The imaging volume may be configured as an imaging chamber, which may have any suitable configuration known in the art. Storage vessel 12 may be configured as a microtiter plate or any other suitable sample container known in the art.

The system also includes single bi-directional pump 14 configured to draw fluid into a storage reservoir and to later expel fluid from the storage reservoir into the imaging volume. Pump 14 may have any suitable configuration known in the art. Since the particles are substantially immobilized during the exposure time as described further herein, pulse-free flow such as that obtained from an expensive syringe pump is not required for the system embodiments described herein. A sufficient reservoir can be formed out of a length of tubing 16 between pump 14 and sample valve 18. Such a reservoir is commonly called a "sample loop." The tubing may have any suitable configuration. The function of sample valve 18 is to connect a sample probe (not shown) to the reservoir when aspirating from storage vessel 12 (e.g., the microtiter plate) and to connect the reservoir to the imaging chamber when dispensing. Sample valve 18 may include any suitable valve known in the art.

Wash valve 20 is utilized at the pump end of the storage reservoir to allow fresh water (or other suitable reagent) from storage vessel 22 to flow to the imaging volume. Wash valve 20 may include any suitable valve known in the art. Note that the sample and wash valves could be combined into a single valve (not shown). Pump 14 may also be configured to transfer the one or more materials and any other fluid in imaging volume 10 to waste vessel 24. Waste vessel 24 may have any suitable configuration known in the art. The embodiment shown in FIG. 5 may be further configured as described herein.

Figure 6:
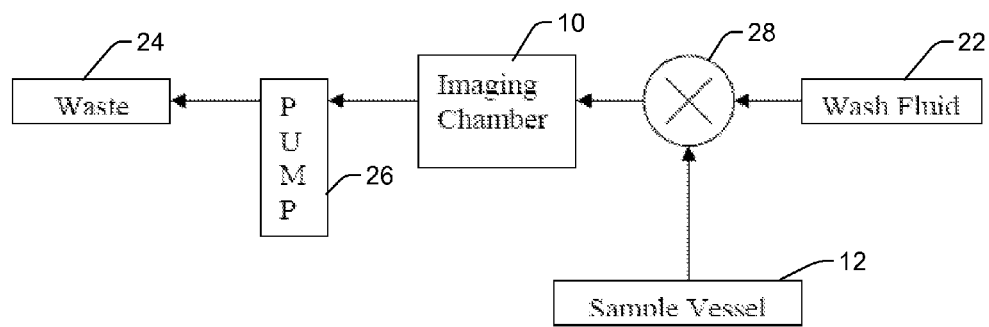

Another embodiment of a system configured to transfer one or more materials to an imaging volume of a measurement device from one or more storage vessels is shown in FIG. 6. In this configuration, the system includes pump 26 configured to draw liquid directly into imaging volume 10 from storage vessel 12 (e.g., the sample probe) and then out to waste vessel 24. Pump 26 may include any suitable pump known in the art such as a peristaltic pump. Imaging volume 10, storage vessel 12, and waste vessel 24 may be configured as described above. Optional valve 28 between storage vessels 12 and 22 (e.g., a microtiter plate or another suitable sample container) and imaging volume 10 may be configured to change positions depending on whether sample is to be transferred to the imaging volume or if wash fluid is to be transferred to the imaging volume (e.g., if the wash function is to be performed). Valve 28 may include any suitable valve known in the art. In addition, storage vessel 22 may be configured as described above.

The embodiment shown in FIG. 6 is advantageous over the embodiment shown in FIG. 5 since this embodiment saves the cost of a temporary reservoir, includes one less valve, and utilizes a pump configured to move fluids in only one direction. A disadvantage of the embodiment shown in FIG. 6 over the embodiment shown in FIG. 5 is the inability of the embodiment shown in FIG. 6 to cleanse the sample probe with wash fluid, without which may lead to increased "carry over" from sample to sample. The embodiment shown in FIG. 6 may be further configured as described herein.

Figure 7:
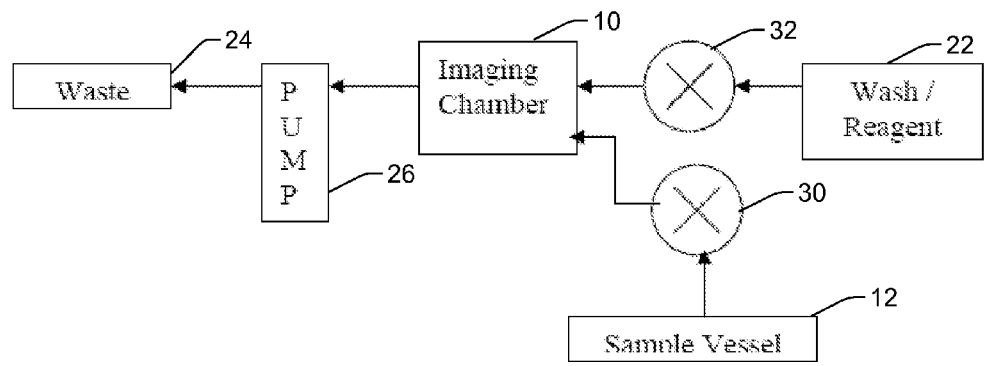

An additional embodiment of a system configured to transfer one or more materials to an imaging volume of a measurement device from one or more storage vessels is shown in FIG. 7. This embodiment has a configuration that is similar to the configuration of the embodiment shown in FIG. 6, with the exception that sample/wash valve 28 of the embodiment shown in FIG. 6 is replaced by two valves 30 and 32. Valves 30 and 32 may include any suitable valves known in the art. For example, valves 30 and 32 may include open/closed type valves configured to separately and simultaneously allow fluid from storage vessels 12 and 22, respectively, to be transferred into imaging volume 10. Storage vessels 12 and 22 and imaging volume 10 may be configured as described herein.

Providing separate wash and sample paths (i.e., one path from storage vessel 12 to imaging volume 10 and another separate path from storage vessel 22 to imaging volume 10) in this manner makes it possible to achieve all of the aspects of the embodiment shown in FIG. 6 and adds the ability to mix wash fluid and/or one or more reagents to the one or more materials to be measured (i.e., the sample solution) as the sample is transferred into imaging volume 10. Mixing wash fluid and/or one or more reagents to the one or more materials (e.g., the sample) as the one or more materials are transferred to the imaging volume may be performed to dilute the sample such that the particles are distributed farther apart within the imaging volume (e.g., farther apart on the floor of the imaging chamber) thereby enabling better statistical separation of the particles, which will result in more accurate measurement of each particle. The embodiment shown in FIG. 7 may be further configured as described herein.

Another embodiment relates to a method for transferring one or more materials to an imaging volume of a measurement device from one or more storage vessels. Transferring the one or more materials may be performed as described further herein. In addition, this method may include any other step(s) described herein. For example, the method may include mixing wash fluid and/or one or more reagents to the one or more materials as the one or more materials are transferred to the imaging volume. Furthermore, this method may be performed by any of the systems described herein (e.g., by the embodiments shown in FIGS. 5-7).

Figure 9:
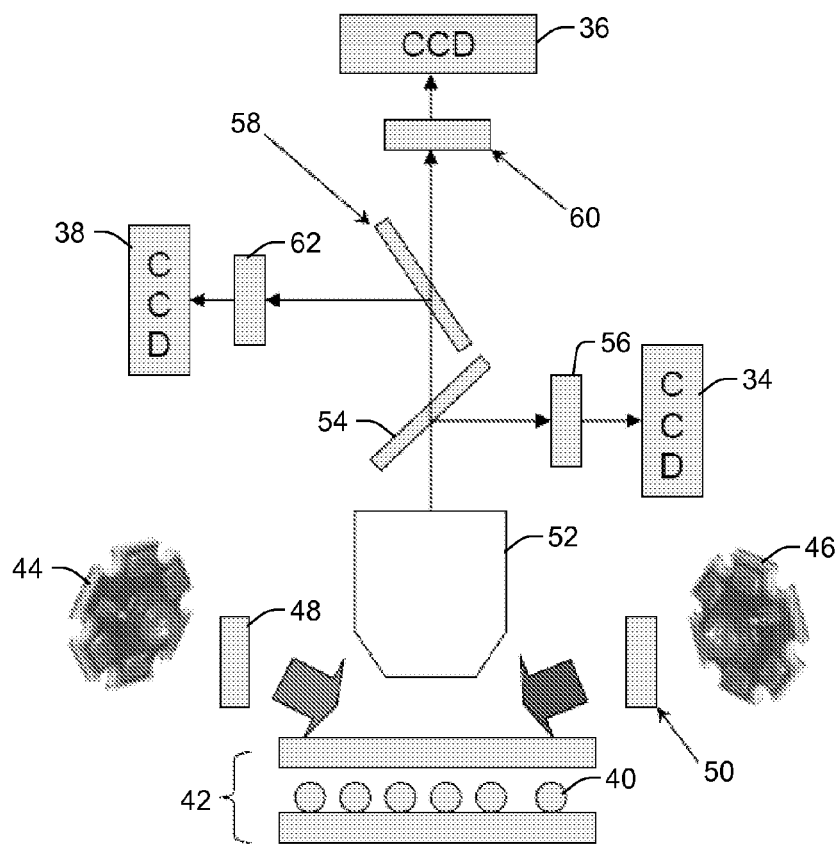
FIGS. 9-15 are schematic diagrams illustrating a side view of various embodiments of a system configured to image one or more materials in an imaging volume of a measurement device.

FIGS. 8-9 illustrate one embodiment of a system configured to image one or more materials in an imaging volume of a measurement device. This system embodiment includes detectors 34, 36, and 38. Detectors 34, 36, and 38 may be CCD cameras or any other suitable imaging devices known in the art. Each of the detectors may have the same configuration or different configurations. Each of the detectors may be configured to detect light (e.g., light fluoresced from particles 40 in imaging volume defined by imaging chamber 42) at a different wavelength or wavelength band. In addition, each of the detectors may be configured to generate images or "capture fluorescent pictures" of particles 40 in imaging chamber 10 (e.g., particles resting on the bottom of imaging chamber 42). Imaging chamber 10 may have any suitable configuration known in the art.

The system also includes light sources 44 and 46 configured to emit light having different wavelengths or different wavelength bands (e.g., one of the light sources may be configured to emit red light and the other light source may be configured to emit green light). The light emitted by light sources 44 and 46 may include, for example, light in any part of the visible wavelength spectrum. Light sources 44 and 46 may include LEDs or any other suitable light sources known in the art. Light sources 44 and 46 are arranged above the periphery of imaging chamber 42. In addition, the light sources are arranged above the imaging chamber such that each light source directs light to particles 40 in imaging chamber 10 at different directions.

The system also includes filters 48 and 50 coupled to light sources 44 and 46, respectfully. Filters 48 and 50 may be bandpass filters or any other suitable spectral filters known in the art. In this manner, the system may use light sources 44 and 46 and filters 48 and 50 to sequentially illuminate the particles with different wavelengths or different wavelength bands of light. For example, red light may be used to excite classification dyes (not shown) that may be internal to the particles, and green light may be used to excite reporter molecules (not shown) coupled to the surface of the particles. Since the classification illumination is dark during reporter measurements (i.e., in the above example, red light is not directed to the particles while green light is directed to the particles), the analyte measurement sensitivity of the system will not be reduced due to crosstalk from out of band light.

The system may also include single lens 52 positioned at the center (or approximately the center) of the illumination "ring." Lens 52 may include any suitable refractive optical element known in the art. Lens 52 is configured to image light scattered and/or fluoresced from the particles onto one or more monochrome CCD detector(s) (e.g., detectors 34, 36, and 38) via one or more optical elements, which may include one or more dichroic and one or more optical bandpass filters. For example, light exiting lens 52 is directed to dichroic filter 54, which may include any suitable dichroic optical element known in the art. Dichroic filter 54 is configured to reflect light of one wavelength or wavelength band and to transmit light of other wavelengths or wavelength bands. Light reflected by dichroic filter 54 is directed to filter 56, which may be a bandpass filter or other suitable spectral filter. Light exiting filter 56 is directed to detector 34.

Light transmitted by dichroic filter 54 is directed to dichroic filter 58, which may include any suitable dichroic optical element known in the art. Dichroic filter 58 may be configured to reflect light of one wavelength or wavelength band and to transmit light of other wavelengths or wavelength bands. Light transmitted by dichroic filter 58 is directed to filter 60, which may be a bandpass filter or other suitable spectral filter. Light exiting filter 60 is directed to detector 36. Light reflected by dichroic filter 58 is directed to filter 62, which may be a bandpass filter or other suitable spectral filter. Light exiting filter 62 is directed to detector 38.

Furthermore, although the system shown in FIG. 9 includes two light sources, it is to be understood that the system may include any suitable number of light sources. For example, as shown in FIG. 8, the system may include four light sources (e.g., light sources 44, 45, 46, and 47) arranged around the periphery of lens 52. Light sources 44, 45, 46, and 47 may include any of the light sources described herein. In this manner, light sources 44, 45, 46, and 47 may be configured to provide an illumination "ring" surrounding lens 52.

Although the system shown in FIGS. 8-9 includes three detectors configured to image light scattered and/or fluoresced from the particles at different wavelengths or wavelength bands, it is to be understood that the system may include two or more detectors. For example, the system may include two or more CCD detectors (and optionally fixed filters) that can be used to simultaneously measure the classification channel(s) and reporter channel(s) thereby providing higher throughput for the measurements along with additional hardware cost.

The system shown in FIGS. 8-9 is, therefore, configured to generate a plurality or series of images representing the fluorescent emission of particles 40 at several wavelengths of interest. In addition, the system may be configured to supply a plurality or series of digital images representing the fluorescence emission of the particles to a processor (i.e., a processing engine). The system may or may not include the processor (not shown). The processor may be configured to acquire (e.g., receive) image data from detectors 34, 36, and 38. For example, the processor may be coupled to detectors 34, 36, and 38 in any suitable manner known in the art (e.g., via transmission media (not shown), each coupling one of the detectors to the processor, via one or more electronic components (not shown) such as analog-to-digital converters, each coupled between one of the detectors and the processor, etc.).

Preferably, the processor is configured to process and analyze these images to determine one or more characteristics of particles 40 such as a classification of the particles and information about a reaction taken place on the surface of the particles. The one or more characteristics may be output by the processor in any suitable format such as a data array with an entry for fluorescent magnitude for each particle for each wavelength. Specifically, the processor may be configured to perform one or more steps of a method for processing and analyzing the images. Examples of methods for processing and analyzing images generated by a system such as that shown in FIGS. 8-9 are illustrated in U.S. Patent Application Ser. No. 60/719,010 entitled "Methods and Systems for Image Data Processing" filed Sep. 21, 2005 by Roth, which is incorporated by reference as if fully set forth herein. The systems described herein may be further configured as described in this patent application. In addition, the methods described herein may include any step(s) of any of the method(s) described in this patent application.

The processor may be a processor such as those commonly included in a typical personal computer, mainframe computer system, workstation, etc. In general, the term "computer system" may be broadly defined to encompass any device having one or more processors, which executes instructions from a memory medium. The processor may be implemented using any other appropriate functional hardware. For example, the processor may include a digital signal processor (DSP) with a fixed program in firmware, a field programmable gate array (FPGA), or other programmable logic device (PLD) employing sequential logic "written" in a high level programming language such as very high speed integrated circuits (VHSIC) hardware description language (VHDL). In another example, program instructions (not shown) executable on the processor to perform one or more steps of the computer-implemented methods described in the above-referenced patent application may be coded in a high level language such as C#, with sections in C++ as appropriate, ActiveX controls, JavaBeans, Microsoft Foundation Classes ("MFC"), or other technologies or methodologies, as desired. The program instructions may be implemented in any of various ways, including procedure-based techniques, component-based techniques, and/or object-oriented techniques, among others.

Program instructions implementing methods such as those described in the above-referenced patent application may be transmitted over or stored on a carrier medium (not shown). The carrier medium may be a transmission medium such as a wire, cable, or wireless transmission link. The carrier medium may also be a storage medium such as a read-only memory, a random access memory, a magnetic or optical disk, or a magnetic tape.

Another embodiment relates to a method for imaging one or more materials in an imaging volume of a measurement device. Imaging the one or more materials may be performed as described further herein. In addition, this method may include any other step(s) described herein. Furthermore, this method may be performed by any of the systems described herein.

Figure 10:
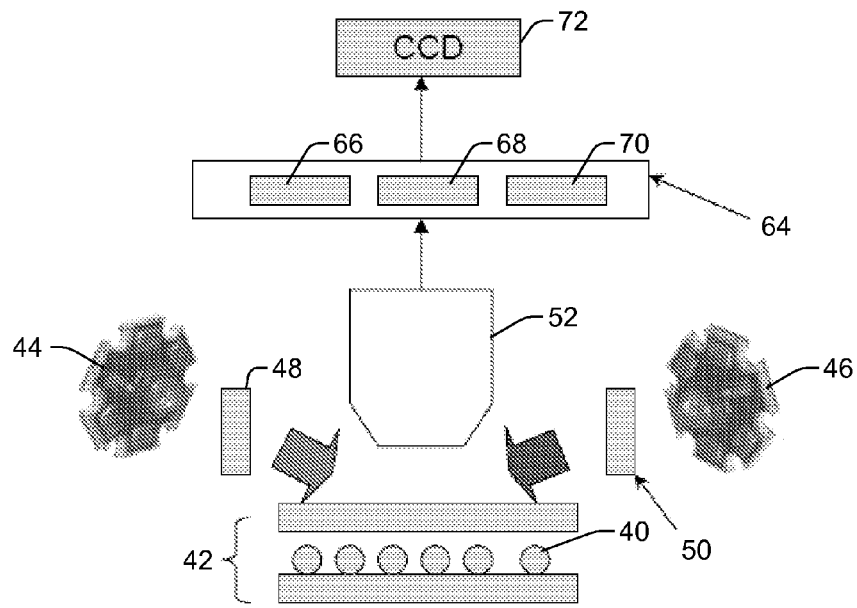

Another embodiment of a system configured to image one or more materials in an imaging volume of a measurement device is shown in FIG. 10. This system embodiment includes imaging chamber 42, light sources 44 and 46, filters 48 and 50, and lens 52, which may be configured as described above with respect to FIGS. 8-9. In this embodiment, however, the system includes substrate 64 that includes filters 66, 68, and 70. Filters 66, 68, and 70 may include bandpass filters or any other suitable spectral filters known in the art. Substrate 64 may include any appropriate substrate known in the art. Substrate 64 may be coupled to one or more devices that are configured to alter a position of the substrate and therefore the filters in the optical path of the light exiting lens 52. For example, the one or more devices may be configured to alter the position of the substrate by rotating the substrate. As such, the substrate and the filters therein may be configured as a circular, rotating filter "wheel." However, the one or more devices may be configured to alter the position of the substrate in any other manner known in the art.

Each of filters 66, 68, and 70 may be configured to transmit light of a different wavelength or a different wavelength band. As such, the wavelength or wavelength band at which an image of particles 40 is formed by detector 72 may vary depending on the position of the substrate and therefore the position of the filters in the optical path of light exiting lens 52. In this manner, a plurality of images of the particles may be formed sequentially by imaging the particles, altering the position of the substrate and therefore the filters, and repeating the imaging and altering steps until images at each wavelength or waveband of interest have been acquired by detector 72. In addition, although three filters are shown in substrate 64 in FIG. 10, it is to be understood that the substrate may include any suitable number of filters. In addition, the system may include two or more such filters arranged in any other suitable configuration such that the system can alter the filter that is in the optical path of light exiting lens 52 in any other manner known in the art. Detector 72 may include any of the detectors described herein such as a CCD array.

The system embodiment shown in FIG. 10 is, therefore, advantageous since the system is configured to use a single detector (e.g., a single CCD detector) with optical filters unique to the wavelengths or wavelength bands of interest (e.g., classification channel 1 (cl1), classification channel 2 (cl2), reporter channel 1 (rp1), etc.) arranged on a circular "filter wheel," which provides a cost effective solution. However, this system is slower (i.e., has a lower throughput) than the system shown in FIGS. 8-9 due to non-simultaneous, sequential exposures used to form the plurality of images. The system shown in FIG. 10 may be further configured as described herein.

Figure 11:
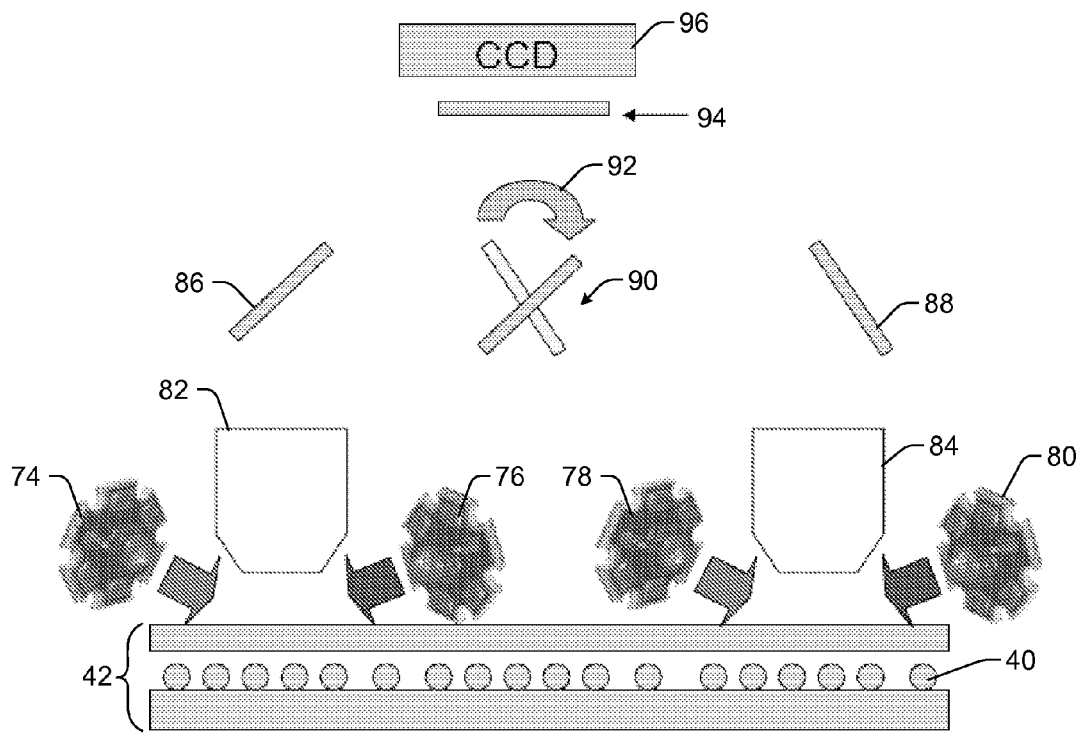

An additional embodiment of a system configured to image one or more materials in an imaging volume of a measurement device is shown in FIG. 11. In this embodiment, the system is configured to have approximately double the imaging area of the systems shown in FIGS. 8-10 and to use a single detector and multiple filters that can be moved into and out of the optical path as described further above. In particular, the system shown in FIG. 11 includes a first set of light sources 74 and 76, which may include any of the light sources described herein. Light sources 74 and 76 are configured such that both light sources direct light to approximately the same area of imaging chamber 42, which may be configured as described herein. The system also includes a second set of light sources 78 and 80, which may include any of the light sources described herein. Light sources 78 and 80 are configured such that both light sources direct light to approximately the same area of imaging chamber 42, which is spaced from the area of the imaging chamber to which light sources 74 and 76 direct light.

The system shown in FIG. 11 also includes lens 82. Lens 82 is configured to collect light from the area of the imaging chamber to which light sources 74 and 76 direct light. The light collected by lens 82 may include fluorescent light and/or scattered light emanating from the particles or material(s) coupled thereto. Lens 82 may be further configured as described herein. The system also includes lens 84 that is configured to collect light from the area of the imaging chamber to which light sources 78 and 80 direct light. The light collected by lens 84 may include fluorescent light and/or scattered light emanating from the particles or material(s) coupled thereto. Lens 84 may be further configured as described herein. Lenses 82 and 84 may be configured similarly or differently.

Light collected by lens 82 is directed to reflective optical element 86, which may be any suitable reflective optical element known in the art such as a mirror. The position of reflective optical element 86 may be relatively fixed. Light collected by lens 84 is directed to reflective optical element 88, which may be any suitable reflective optical element known in the art such as a mirror. The position of reflective optical element 88 may be relatively fixed. Reflective optical elements 86 and 88 may both be configured to direct light to reflective optical element 90, which may include any suitable reflective optical element known in the art such as a mirror. Reflective optical element 90 may be coupled to one or more devices (not shown) that are configured to alter a position of the reflective optical element as shown by arrow 92. The one or more devices may include any suitable device(s) known in the art. In this manner, reflective optical element 90 may be configured as a "flip mirror," and the position of the mirror may be altered depending on which area of the imaging chamber is being imaged.

In particular, depending on the position of reflective optical element 90, light from reflective optical element 86 or reflective optical element 88 will be directed to substrate 94. Substrate 94 may be configured as described above with respect to substrate 64. In particular, substrate 94 may include two or more filters (not shown in FIG. 11), and the position of the substrate and therefore the two or more filters with respect to reflective optical element 90 may be altered depending on the wavelength or wavelength band at which an image is being formed. Light transmitted by the two or more filters is directed to detector 96, which may include a CCD detector or any other detector described herein.

The system shown in FIG. 11 is, therefore, advantageous since this configuration doubles the imaging area and uses a single detector (e.g., a single CCD) and multiple bandpass filters on a rotating wheel. As described above, reflective optical element 90 (e.g., a mirror) flips between positions to direct the fluorescent light from lenses 82 and 84 to detector 96 in successive exposures. As such, another advantage of the optical system shown in FIG. 11 is that double the particles can be brought into the imaging chamber at once compared to the number of particles that can be brought into the imaging chambers of the systems shown in FIGS. 4-6 thereby saving the time necessary to flip valves, etc. The system shown in FIG. 11 may be further configured as described herein.

Figure 12:
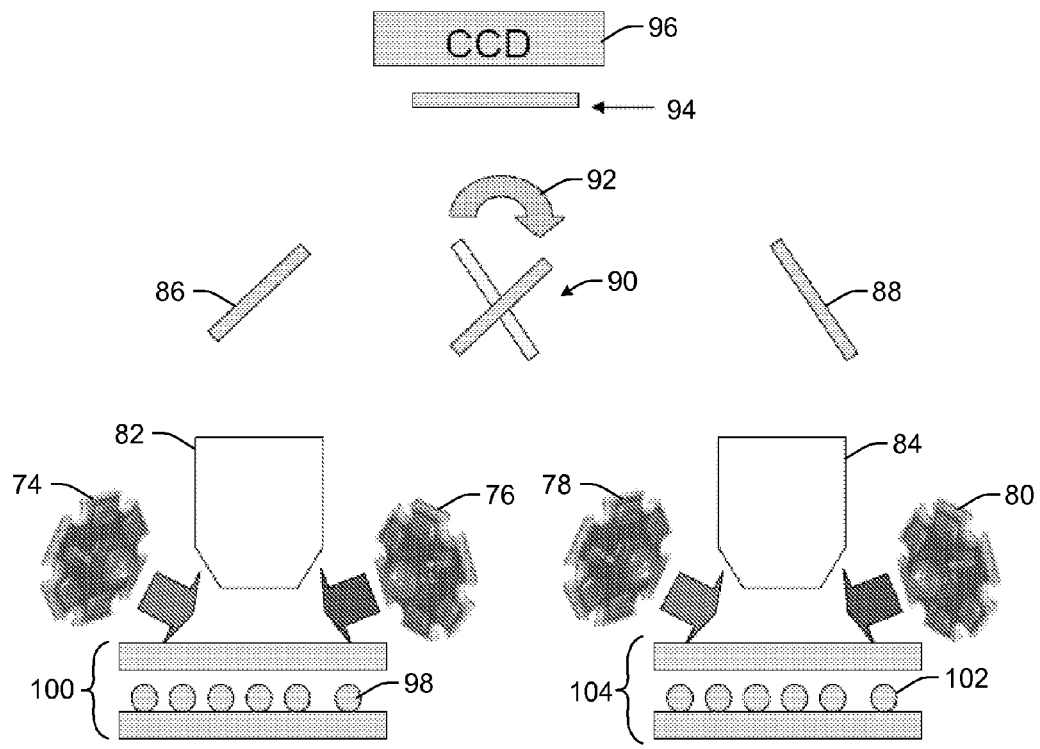

A further embodiment of a system configured to image one or more materials in an imaging volume of a measurement device is shown in FIG. 12. This embodiment of the system is similar to that shown in FIG. 11 except that this embodiment is configured to image particles that are separated into two separate imaging chambers. In particular, light sources 74 and 76 are configured to direct light to particles 98 in imaging chamber 100, and lens 82 is configured to collect light from particles 98 in imaging chamber 100. Light sources 78 and 80 are configured to direct light to particles 102 in imaging chamber 104, and lens 84 is configured to collect light from particles 102 in imaging chamber 104. Imaging chambers 100 and 104 may be configured as described herein. In addition, imaging chambers 100 and 104 may be configured similarly or differently. The system may also be advantageously configured such that while particles are being loaded into one of the imaging chambers, the system can be imaging light scattered and/or fluoresced from particles in the other imaging chamber thereby saving acquisition time. The system embodiment shown in FIG. 12 may be further configured as described herein.

Figure 13:
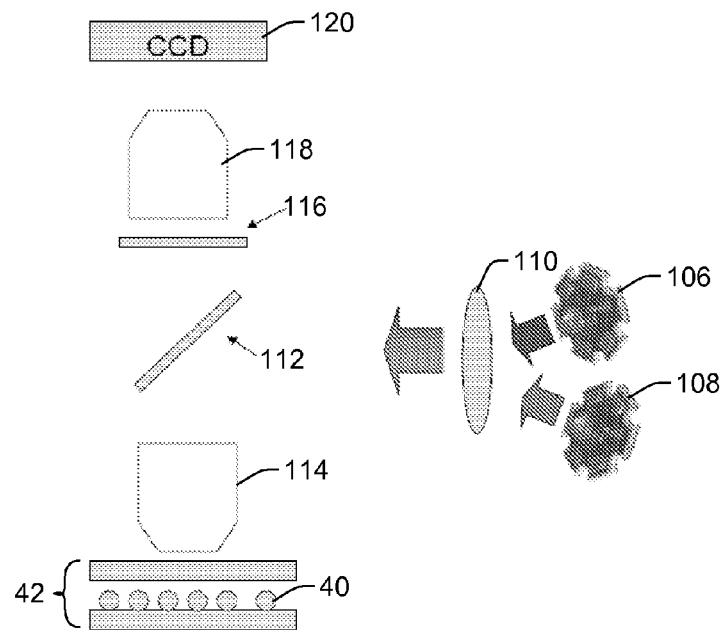

Another embodiment of a system configured to image one or more materials in an imaging volume of a measurement device is shown in FIG. 13. This system includes light sources 106 and 108, which may include any of the light sources described herein. Light sources 106 and 108 are configured to direct light to refractive optical element 110, which may include any suitable refractive optical element known in the art. Light exiting refractive optical element 110 is directed to dichroic optical element 112, which is configured to reflect light from refractive optical element 110 to refractive optical element 114. Dichroic optical element 112 may include any suitable dichroic optical element known in the art such as a dichromatic mirror. Refractive optical element 114 may include any suitable refractive optical element known in the art such as a lens. Refractive optical element 114 is configured to direct light from dichroic optical element 112 to particles 40 located in imaging chamber 42, which may be configured as described herein.

Fluorescent and/or scattered light emanating from particles 40 is collected by refractive optical element 114, which directs the fluorescent and/or scattered light to dichroic optical element 112. Dichroic optical element 112 is configured to transmit the fluorescent and/or scattered light. Therefore, the system shown in FIG. 13 is configured to illuminate the particles through refractive optical element 114 (e.g., an imaging objective lens) via dichroic optical element 112 (e.g., a dichromatic mirror) that is configured to separate the excitation and the emission light based upon wavelength. Such a configuration of the system is advantageous since it provides more uniform illumination across the field of view of the system.

The light transmitted by dichroic optical element 112 is directed to substrate 116, which may include a plurality of filters (not shown in FIG. 13). Substrate 116 and the plurality of filters may be configured as described herein. Light exiting substrate 116 may be directed to optional refractive optical element 118, which may include any suitable refractive optical element known in the art such as a lens. Light exiting optional refractive optical element 1118, or substrate 116 if refractive optical element 118 is not included in the system, is directed to detector 120, which may include any of the detectors described herein. The system shown in FIG. 13 may be further configured as described herein.

An additional embodiment (not shown) of a system configured to image one or more materials in an imaging volume of a measurement device includes a light source configured to emit light that the system is configured to scan across the imaging volume. For example, the system may include an optical element that is configured to alter the direction of the light from the light source such that the light scans over the imaging chamber. In such a system, the light source and/or the imaging chamber may or may not be substantially stationary. Alternatively, the system may be configured to alter a position of the light source (and optical element(s) associated with the light source) while the imaging chamber is substantially stationary such that the light scans over the imaging chamber. In another alternative, the system may be configured to alter a position of the imaging chamber while the light source (and optical element(s) associated with the light source) is substantially stationary such that the light scans over the imaging chamber. In a further alternative, the system may be configured to alter a position of the light source (and optical element(s) associated with the light source) and the imaging chamber such that the light scans over the imaging chamber. The system may be configured to alter a position of the light source (and optical element(s) associated with the light source) and/or a position of the imaging chamber in any manner known in the art.

In some such embodiments, the light source may include a laser, which may include any suitable laser known in the art. In addition, the system may include a single detector and optical filters, and the system may be configured to position one of the optical filters in front of the detector depending on the wavelength or wavelength band at which an image is being formed. In this manner, different images of light scattered and/or fluoresced from the particles may be formed at different wavelengths or wavelength bands while different optical filters are positioned in front of the detector. The detector may include any of the detectors described herein. In addition, the optical filters may include any of the optical filters described herein. Furthermore, the system may be configured to position one of the optical filters in front of the detector as described herein. Therefore, this configuration may use a scanning laser(s) and a single detector with optical filters unique to the wavelengths or wavelength bands of interest (cl1, cl2, classification channel 3 (cl3), rp1, etc.).

Instead of illuminating the entire field of beads simultaneously, therefore, the system may be configured such that the laser(s) scan a spot smaller in diameter than the beads across the image plane thereby illuminating each particle separately. An advantage of this embodiment over configurations that include a two-dimensional CCD array is that the light measured at any time is guaranteed as being sourced from a single bead (assuming the beads are far enough apart). In contrast, in the flooded field (i.e., flood illumination) systems shown in FIGS. 4-6, light detected by each pixel element of the detector (e.g., a CCD) may include some contribution from beads outside the area intended to be imaged by each pixel element. This embodiment of the system may be further configured as described herein.

A further embodiment (not shown) of a system configured to image one or more materials in an imaging volume of a measurement device includes a light source configured to emit light that the system is configured to scan across the imaging volume. The system may be configured to scan the light across the imaging volume as described herein. Like the system embodiment described above, this configuration may use a scanning laser(s). Therefore, instead of illuminating the entire field of beads simultaneously, the laser(s) scan a spot across the image plane illuminating each particle separately. However, unlike the system embodiment described above, the system may include one or more PMT detector(s) and optical filters unique to the wavelength bands of interest (cl1, cl2, cl3, rp1, etc.). The optical filters may be positioned in front of the one or more PMT detector(s) as described above. If the number of PMTs included in the system is less than the number of wavelengths or wavelength bands at which an image is to be acquired, the filters for one or more of the PMTs may be arranged as described herein (e.g., on a circular filter wheel), and the desired filter can be rotated into view before the scan commences. This embodiment of the system may be further configured as described herein.

Figure 14:
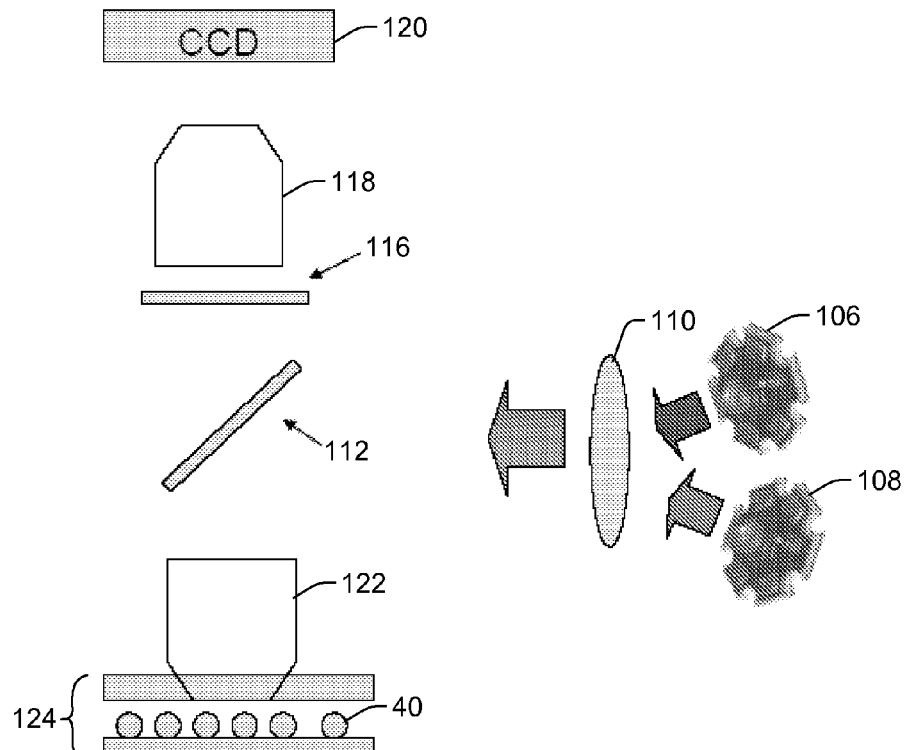

An additional embodiment of a system configured to image one or more materials in an imaging volume of a measurement device is shown in FIG. 14. The system shown in FIG. 14 may be configured as described above with respect to FIG. 13 except that FIG. 14 includes a refractive optical element that is different than refractive optical element 114 of the system of FIG. 13 and a different imaging chamber than the system of FIG. 13. In particular, the system shown in FIG. 14 includes refractive optical element 122, which is coupled to imaging chamber 124. For instance, refractive optical element 122 may be positioned in an opening formed in imaging chamber 124 such that the surfaces of refractive optical element 122 and imaging chamber 124 proximate to particles 40 are located in substantially the same plane. In addition, the surfaces of refractive optical element 122 and imaging chamber 124 that are in contact with each other may be joined in some manner. Refractive optical element 122 and imaging chamber 124 may be further configured as described herein.

The embodiment of the system shown in FIG. 14 is advantageous since this configuration employs a lens that is embedded in the imaging chamber to allow for maximum numerical aperture and thus maximum light collection from the sample. As described further above, the particles are illuminated through refractive optical element 122 (e.g., an imaging objective lens) via dichroic optical element 112 (e.g., a dichromatic mirror) that separates the excitation and the emission wavelengths. The embodiment of the system shown in FIG. 14 may be further configured as described herein.

Figure 15:
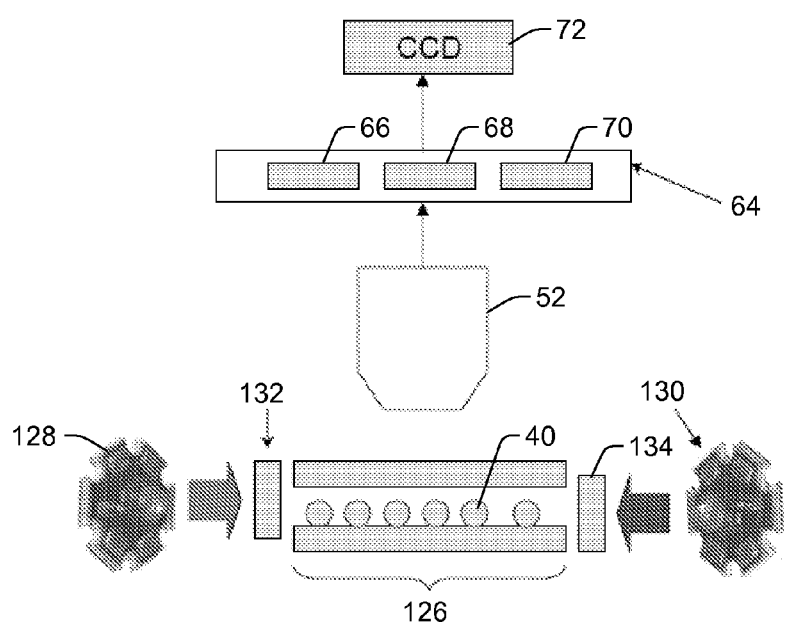

An additional embodiment of a system configured to image one or more materials in an imaging volume of a measurement device is shown in FIG. 15. In this system, imaging chamber 126 is configured as a waveguide imaging chamber. The waveguide imaging chamber may be configured as described herein. As shown in FIG. 15, the system includes light sources 128 and 130. Light sources 128 and 130 may include any of the light sources described herein. Light sources 128 and 130 are configured to direct light to sides of imaging chamber 126 as opposed to a top surface of imaging chamber 126 as in the above-described embodiment configurations. In some embodiments, the system includes filters 132 and 134 positioned between light sources 128 and 130, respectively, and the imaging chamber. Filters 132 and 134 may include bandpass filters or any other suitable filters known in the art.

The system may also include lens 52, substrate 64 that includes filters 66, 68, and 70, and detector 72, each of which may be configured as described above with respect to FIG. 10. However, unlike the system shown in FIG. 10, the system shown in FIG. 15 employs a waveguide imaging chamber design to illuminate particles 40. This illumination configuration allows lens 52 in the system of FIG. 15 to have a relatively short working distance with a larger numerical aperture than lens 52 in the system of FIG. 10. Such a lens will collect more light from the beads thereby decreasing exposure time. This illumination configuration may also limit the amount of incident light from the light sources collected by the lens. The embodiment of the system shown in FIG. 15 may be further configured as described herein.

Figure 16:
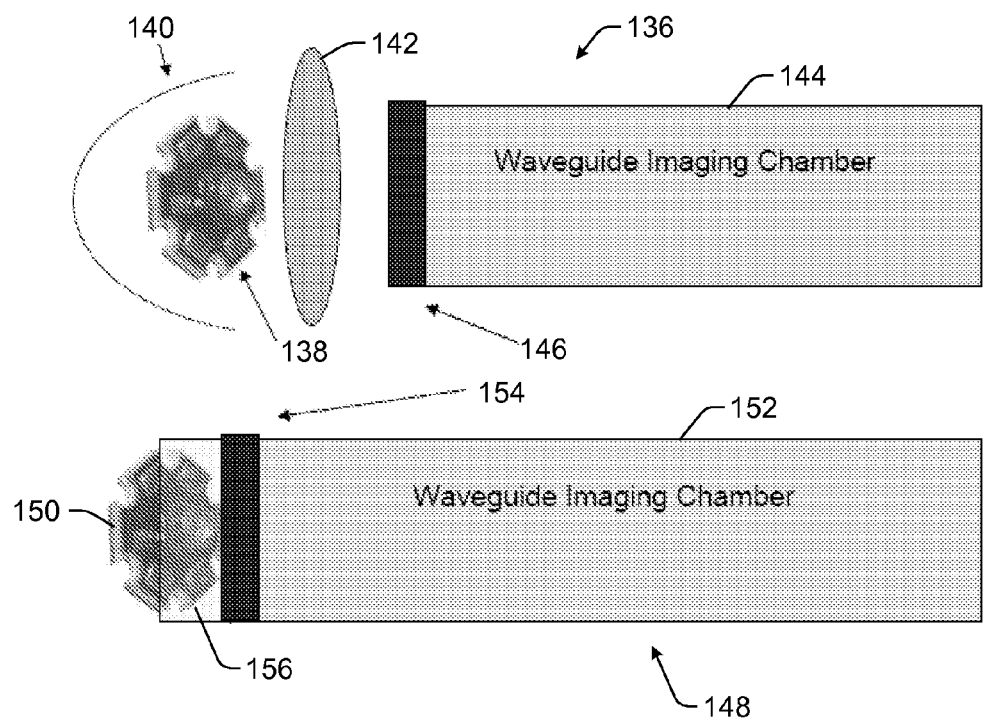
FIGS. 16-17 are schematic diagrams illustrating a side view of various embodiments of an illumination subsystem that may be included in embodiments of a system configured to image one or more materials in an imaging volume of a measurement device described herein.
Figure 17:
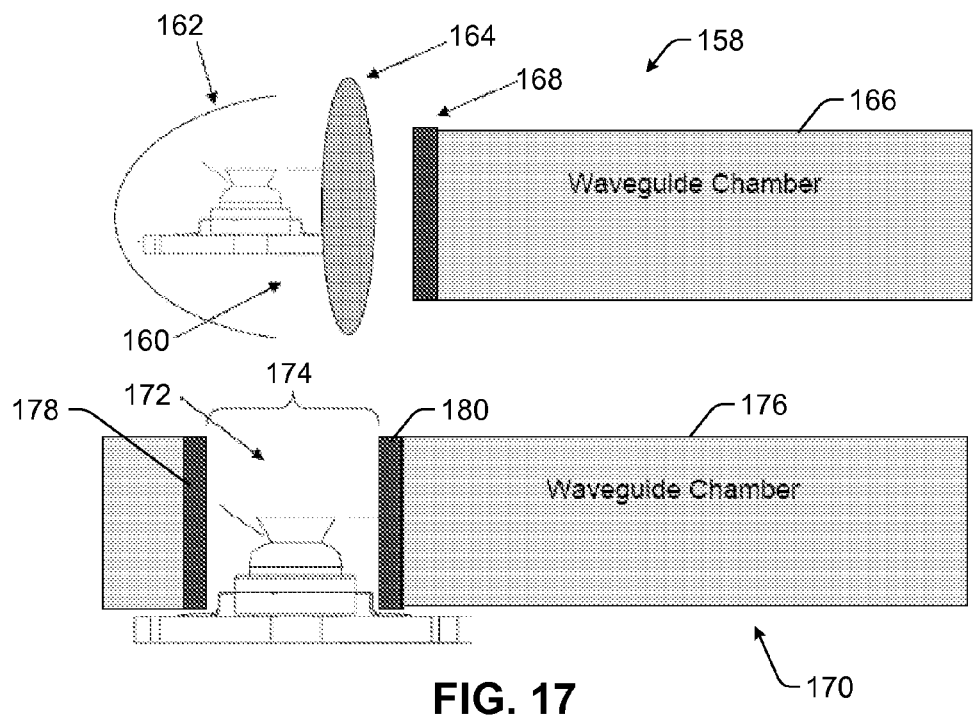

FIGS. 16-17 illustrate various embodiments of an illumination subsystem that may be included in embodiments of a system configured to image one or more materials in an imaging volume of a measurement device described herein. In particular, the illumination subsystems shown in FIGS. 16-17 include light sources (e.g., LEDs) coupled to a waveguide imaging chamber in several possible manners. For example, illumination subsystem 136 includes light source 138 that may include a Lambertian LED. The illumination subsystem also includes reflective optical element 140 and refractive optical element 142, which are configured to focus light from light source 138 to waveguide imaging chamber 144. Reflective optical element 140 may include any suitable reflective optical element known in the art. Refractive optical element 142 may include any suitable refractive optical element known in the art such as a focusing lens. The illumination subsystem may also include filter 146, which may be used as an excitation filter and may include any suitable filter described herein or known in the art. In this manner, illumination subsystem 136 may use a reflective optical element and/or a refractive optical element (e.g., a lens) to capture light (e.g., Lambertian LED light) and focus the light onto the excitation filter or side of the waveguide imaging chamber. This illumination subsystem embodiment may be further configured as described herein.

Illumination subsystem 148 shown in FIG. 16 includes light source 150 that may include a Lambertian LED. In this illumination subsystem, light source 150 is coupled (e.g., butt coupled) to waveguide imaging chamber 152 such that a surface of the light source is in contact with waveguide imaging chamber 152 or filter 154 if this filter is included in the illumination subsystem. Filter 154 may be used as an excitation filter and may include any suitable filter described herein or known in the art. In some embodiments, index matching fluid and/or epoxy 156 is used to couple light source 150 to waveguide imaging chamber 152 or filter 154. Index matching fluid and/or epoxy 156 may include any suitable fluid and/or epoxy known in the art. The index matching fluid and/or epoxy may be used to improve the light coupling from the light source into the waveguide. This illumination subsystem embodiment may be further configured as described herein.

Illumination subsystem 158 shown in FIG. 17 includes light source 160 that may be a side emitting LED. Illumination subsystem 158 also includes reflective optical element 162 and refractive optical element 164, which are configured to focus light from light source 160 to waveguide imaging chamber 166. Reflective optical element 162 may include any suitable reflective optical element known in the art. Refractive optical element 164 may include any suitable refractive optical element known in the art such as a focusing lens. The illumination subsystem may also include filter 168, which may be used as an excitation filter and may include any suitable filter described herein or known in the art. In this manner, illumination subsystem 158 may use a reflective optical element and/or a refractive optical element (e.g., a lens) to capture light (e.g., edge emitting LED light) and focus the light onto the excitation filter or side of the waveguide imaging chamber. This illumination subsystem embodiment may be further configured as described herein.

Illumination subsystem 170 shown in FIG. 17 includes light source 172 that may be a side emitting LED. Light source 172 is disposed in through hole 174 formed in waveguide imaging chamber 176. Therefore, this illumination subsystem may couple a light source (e.g., an edge emitting LED) to a waveguide imaging chamber using a through hole in the waveguide imaging chamber. The illumination subsystem may also include filters 178 and 180, which may be used as excitation filters and may include any suitable filters described herein or known in the art. This illumination subsystem embodiment may be further configured as described herein.

Figure 18:
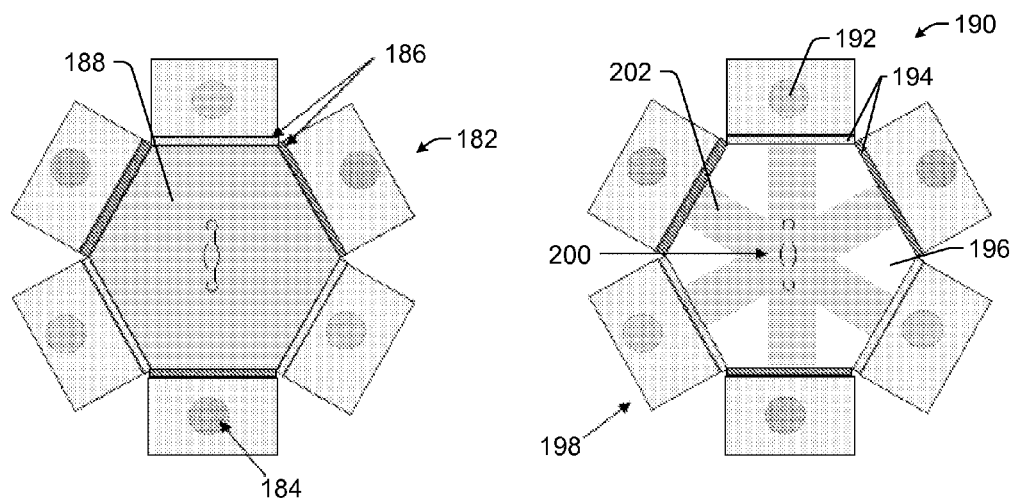
FIGS. 18-20 are schematic diagrams illustrating a top view of various embodiments of an illumination subsystem that may be included in embodiments of a system configured to image one or more materials in an imaging volume of a measurement device described herein.
Figure 19:
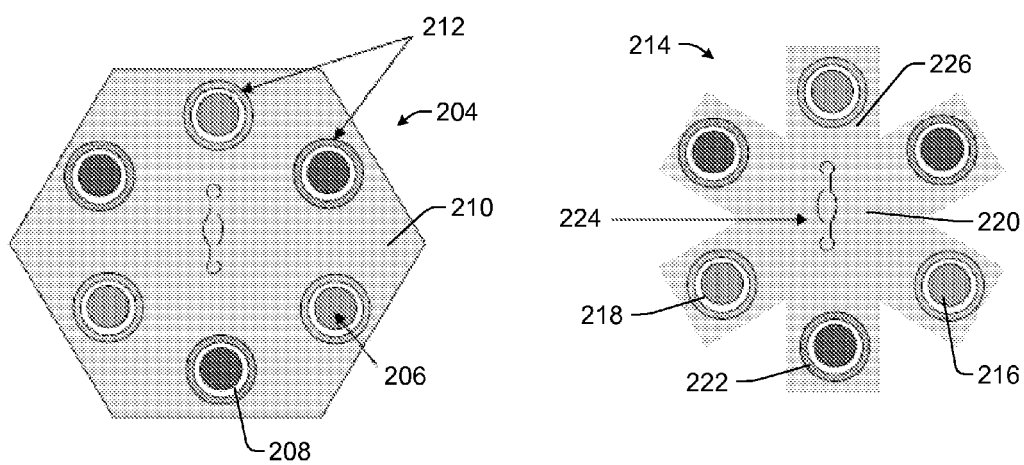

FIGS. 18-19 illustrate various embodiments of an illumination subsystem that may be included in embodiments of a system configured to image one or more materials in an imaging volume of a measurement device described herein. In these illumination subsystems, the waveguide imaging chamber is coupled to multiple light sources (e.g., LEDs). FIG. 18-19 show a top down view of some of these designs using the waveguide coupling described in FIGS. 16-17. For example, illumination subsystem 182 shown in FIG. 18 includes light sources 184, which may be Lambertian LEDs or edge emitting LEDs. Filters 186 may be disposed between each light source and waveguide imaging chamber 188. Filters 186 may include any of the filters described herein or known in the art. Since illumination subsystem 182 is shown to include six light sources arranged around a hexagonal shaped waveguide imaging chamber, illumination subsystem 182 is configured to have a hexagonal design with the edge coupling described above. However, the shape of the waveguide imaging chamber can be varied from a simple rectangle, to more complicated triangles, pentagons, hexagons, etc. to incorporate more light sources. This illumination subsystem is advantageous because three light sources configured to emit light of one color and three light sources configured to emit light of another color (i.e., each wavelength or wavelength band) can be coupled to the waveguide imaging chamber. Such an illumination subsystem configuration increases the intensity of the light directed to the sample and provides substantially uniform illumination. Illumination subsystem 182 may be further configured as described herein.

Illumination subsystem 190 shown in FIG. 18 includes light sources 192, which may be Lambertian LEDs or edge emitting LEDs. Filters 194 may be disposed between each light source and waveguide imaging chamber 196. Filters 194 may include any of the filters described herein or known in the art. The illumination subsystem may also include reflective optical elements and/or refractive optical elements 198, which may be configured to focus light from light sources 192 to filters 194 or the surface of waveguide imaging chamber 196 if the filters are not included in the illumination subsystem. The reflective optical elements and/or refractive optical elements may include any such suitable optical element(s) known in the art. Bead chamber 200 is disposed within waveguide imaging chamber 196. Bead chamber 200 may have any suitable configuration.

Since illumination subsystem 190 is shown to include six light sources arranged around a hexagonal shaped waveguide imaging chamber, illumination subsystem 190 is configured to have a hexagonal design with the edge coupling described above. In addition, illumination subsystem 190 is configured to direct the light from the light sources to bead chamber 200 across three intersecting rectangles 202 within the hexagonal shaped waveguide imaging chamber to better confine the light (e.g., the LED light) to the bead chamber. However, the shape of the waveguide imaging chamber can be varied from a simple rectangle, to more complicated triangles, pentagons, hexagons, etc. to incorporate more light sources. This illumination subsystem is also advantageous because three light sources configured to emit light of one color and three light sources configured to emit light of another color (i.e., each wavelength or wavelength band) can be coupled to the waveguide imaging chamber. Such an illumination subsystem configuration increases the intensity of the light directed to the sample and provides substantially uniform illumination. Illumination subsystem 190 may be further configured as described herein.

Illumination subsystem 204 shown in FIG. 19 includes light sources 206, which may be edge emitting LEDs. Light sources 206 are disposed in through holes 208 formed in waveguide imaging chamber 210. Filters 212 may be disposed between each light source and waveguide imaging chamber 210. Filters 212 may include any of the filters described herein or known in the art. Since illumination subsystem 204 is shown to include six light sources arranged around a hexagonal shaped waveguide imaging chamber, illumination subsystem 204 is configured to have a hexagonal design with through hole coupling of light sources such as edge emitting LEDs described above. However, the shape of the waveguide imaging chamber can be varied from a simple rectangle, to more complicated triangles, pentagons, hexagons, etc. to incorporate more light sources. This illumination subsystem is advantageous because three light sources configured to emit light of one color and three light sources configured to emit light of another color (i.e., each wavelength or wavelength band) can be coupled to the waveguide imaging chamber. Such an illumination subsystem configuration increases the intensity of the light directed to the sample and provides substantially uniform illumination. Illumination subsystem 204 may be further configured as described herein.

Illumination subsystem 214 shown in FIG. 19 includes light sources 216, which may be edge emitting LEDs. Light sources 216 are disposed in through holes 218 formed in waveguide imaging chamber 220. Filters 222 may be disposed between each light source and waveguide imaging chamber 220. Filters 222 may include any of the filters described herein or known in the art. Bead chamber 224 is disposed within waveguide imaging chamber 220. Bead chamber 224 may have any suitable configuration. Since illumination subsystem 214 is shown to include six light sources arranged around a hexagonal shaped waveguide imaging chamber, illumination subsystem 214 is configured to have a hexagonal design with the edge coupling described above. In addition, illumination subsystem 214 is configured to direct the light from the light sources to bead chamber 224 across three intersecting rectangles 226 within the hexagonal shaped waveguide imaging chamber to better confine the light (e.g., LED light) to the bead chamber. However, the shape of the waveguide imaging chamber can be varied from a simple rectangle, to more complicated triangles, pentagons, hexagons, etc. to incorporate more light sources. This illumination subsystem is also advantageous because three light sources configured to emit light of one color and three light sources configured to emit light of another color (i.e., each wavelength or wavelength band) can be coupled to the waveguide imaging chamber. Such an illumination subsystem configuration increases the intensity of the light directed to the sample and provides substantially uniform illumination. Illumination subsystem 214 may be further configured as described herein.

Figure 20:
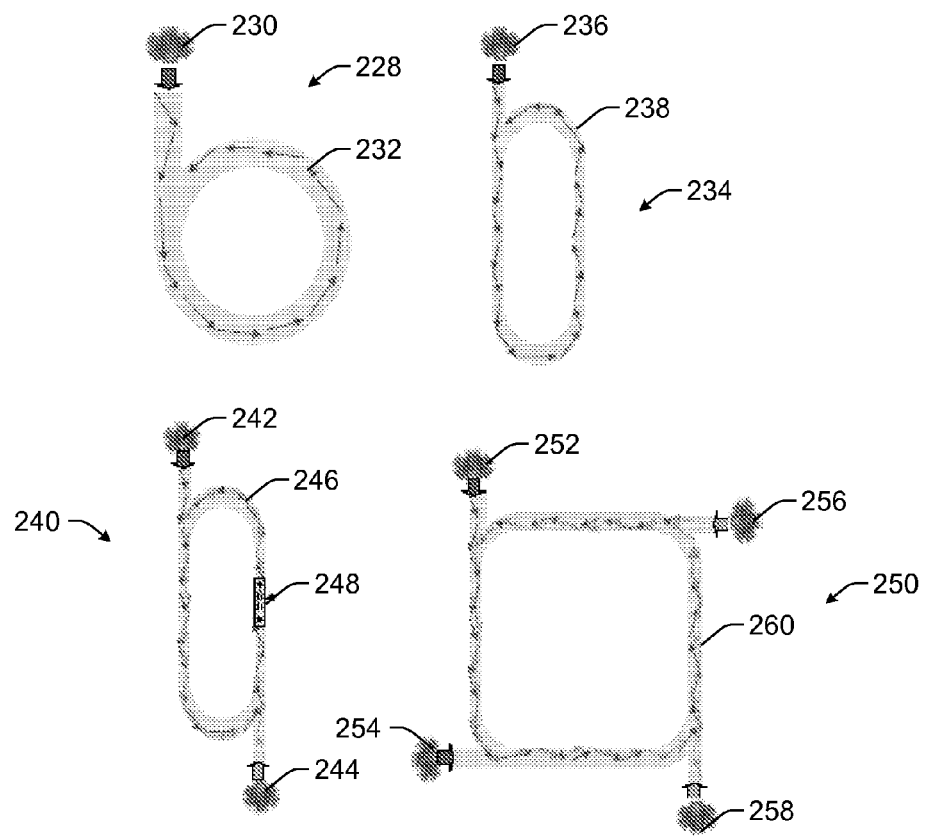

FIG. 20 illustrates various embodiments of an illumination subsystem that may be included in embodiments of a system configured to image one or more materials in an imaging volume of a measurement device described herein. In the embodiments shown in FIG. 20, the waveguide imaging chamber is configured to allow each photon to make more then one pass by the bead chamber. For example, illumination subsystem 228 includes light source 230, which may include any of the light sources described herein. Light source 230 is coupled to ring waveguide imaging chamber 232 such that light emitted by light source 230 enters waveguide imaging chamber 232. By using a ring waveguide imaging chamber design, the photons that are not absorbed by the beads on the first pass will travel around the ring and come back to the sample again. Such a waveguide imaging chamber configuration can greatly increase the intensity of the light on the beads. In addition, such a waveguide imaging chamber configuration will allow for shorter exposure times and the use of fewer light sources. Illumination subsystem 228 may be further configured as described herein.

The basic ring waveguide imaging chamber included in illumination subsystem 228 can be expanded to an oval approach to allow for the insertion of one or more bead chamber regions. For example, as shown in FIG. 20, illumination subsystem 234 includes light source 236 that may include any of the light sources described herein. Light source 236 is coupled to oval waveguide imaging chamber 238 such that light emitted by light source 236 enters waveguide imaging chamber 238. Illumination subsystem 228 may be further configured as described herein.

Multiple light sources may also be coupled to an oval waveguide imaging chamber to allow light from two or more excitation sources to be coupled into the waveguide imaging chamber. For example, as shown in FIG. 20, illumination subsystem 240 includes light sources 242 and 244, which may include any of the light sources described herein. Light sources 242 and 244 are coupled to oval waveguide 246 at different positions within the waveguide imaging chamber such that the light emitted by light sources 242 and 244 enters waveguide imaging chamber 246 at different positions. As further shown in FIG. 20, waveguide imaging chamber 246 includes bead chamber 248 in which beads may be disposed during the measurements such that the beads are illuminated by light from light sources 242 and 244 coupled into the waveguide imaging chamber. Illumination subsystem 240 may be further configured as described herein.

The oval waveguide imaging chamber can also be expanded to other shapes, like a triangle, a square, a pentagon, a hexagon, etc. For example, as shown in FIG. 20, illumination subsystem 250 includes light sources 252, 254, 256, and 258, which may include any of the light sources described herein. Light sources 252, 254, 256, and 258 are coupled to square waveguide imaging chamber 260 at different positions within the waveguide imaging chamber such that the light emitted by light sources 252, 254, 256, and 258 enters waveguide imaging chamber 260 at different positions. Illumination subsystem 250 may be further configured as described herein.

One embodiment of a system configured to substantially immobilize one or more materials in an imaging volume of a measurement device is shown in FIG. 21. This embodiment of the system includes the system configured to image one or more materials in an imaging volume of a measurement device shown in FIG. 10. In addition, this system includes magnetic element 262 positioned on the side of imaging chamber 10 opposite the optics of the system. Magnetic element 262 may include any suitable magnetic element known in the art such as a permanent magnet or an electromagnet that can be used to generate a suitable magnetic field. In this manner, dyed particles with embedded magnetite may be used in the embodiments described herein such that the particles can be substantially immobilized in imaging chamber 10 (e.g., at the bottom of the chamber) using a magnetic field generated by magnetic element 262 at the back side of the chamber. Although magnetic element 262 is shown spaced from imaging chamber 10 in FIG. 21, as shown in FIG. 8, magnetic element 264 may be in contact with (or coupled to) imaging chamber 10 on the side of the imaging chamber opposite the optical elements of the system. Magnetic element 264 may be further configured as described above. In addition, although FIGS. 8 and 21 show one magnetic element positioned proximate the imaging chamber, it is to be understood that the system may include more than one magnetic element, each of which is positioned proximate the side of the imaging chamber opposite the optics of the system.

After signal acquisition by the measurement device, the magnetic field may be removed (e.g., by using a solenoid to move a permanent magnet or by turning an electromagnet on and off with a switch), and the particles may exit the imaging chamber, while new particles from the next sample are brought into the chamber. The particles in the imaging chamber may be removed and particles may be introduced to the imaging chamber using any of the embodiments described herein. The system shown in FIG. 21 may be further configured as described herein.

Figure 22:
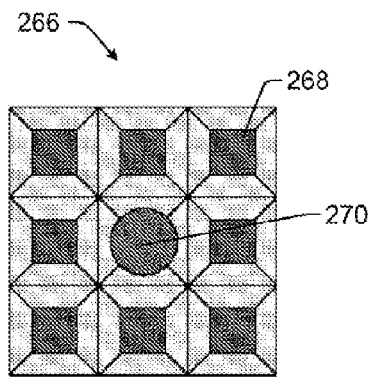
FIGS. 22-23 are schematic diagrams illustrating a top view of various embodiments of a substrate on which one or more materials can be substantially immobilized in an imaging volume of a measurement device.

The simplest imaging chamber design is an imaging chamber that has a relatively smooth internal surface on the side of the imaging chamber proximate the magnetic element such that the beads are randomly distributed across this internal surface as the magnet pulls them down. However, the imaging chamber can also be designed to "hold" the beads in particular spots when the magnetic field is applied. For example, internal surface 266 of an imaging chamber shown in FIG. 22 has a square pattern of etched recesses 268 formed therein such that bead 270 is disposed in one of the etched recesses upon application of a magnetic field as described above. Therefore, etched recesses 268 assist in separating the beads as the magnetic field is applied. In addition, the "etched" recesses may be formed by an etching process or any other suitable process known in the art. Furthermore, the configuration and arrangement of the etched recesses may vary depending on, for example, the size of the beads and the selected spacing between the beads.

Figure 23:
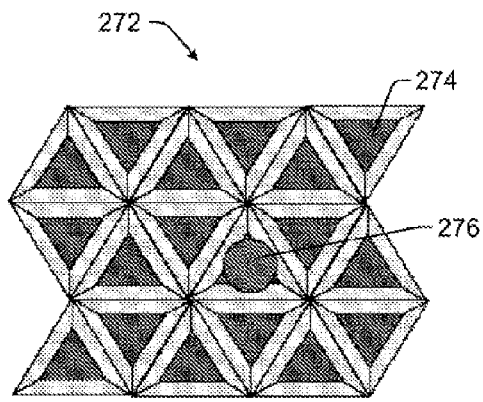

In another example, internal surface 272 of an imaging chamber shown in FIG. 23 has a triangle pattern of etched recesses 274 such that bead 276 is disposed in one of the etched recesses upon application of a magnetic field as described above. Therefore, etched recesses 274 assist in separating the beads as the magnetic field is applied. In addition, the "etched" recesses may be formed by an etching process or any other suitable process known in the art. Furthermore, the configuration and arrangement of the etched recesses may vary depending on, for example, the size of the beads and the selected spacing between the beads. Although etched recesses 268 and 274 shown in FIGS. 22 and 23, respectively, are two-dimensional in the sense that the beads are confined by the recesses in two dimensions, these recesses can be replaced by trenches or any other suitable recesses that are configured to confine the beads in only one direction.

Figure 24:
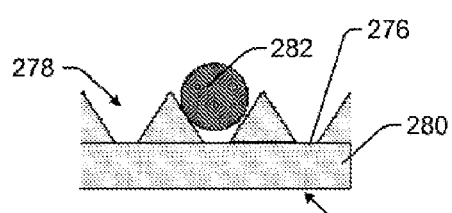
FIGS. 24-25 are schematic diagrams illustrating a side view of various embodiments of a substrate on which one or more materials can be substantially immobilized in an imaging volume of a measurement device.
Figure 25:
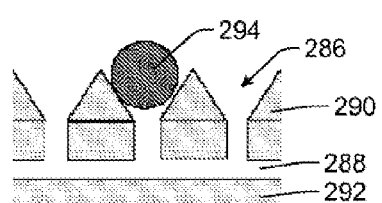

As shown in FIG. 24, bottom 276 of recessed regions 278 can be closed in the sense that there is no opening between bottom 276 of recessed regions 278 and substrate 280 that forms one outer wall of the imaging chamber. Recessed regions 278 may include any of the recessed regions described above. As further shown in FIG. 20, bead 282 becomes confined in recessed region 278 when a magnetic field is applied to side 284 of the imaging chamber. Although the closed recessed regions shown in FIG. 24 are a simpler design, as shown in FIG. 25, recessed regions 286 can be formed with openings 288 between the bottom of structures 290 that form the recessed regions and substrate 292 that forms the outer wall of the imaging chamber. Openings 288 may be configured to allow for flow of wash fluid from behind the beads (e.g., bead 294) such that the wash fluid cannot force the beads out of the recessed regions.

Still another embodiment relates to a method for substantially immobilizing one or more materials in an imaging volume of a measurement device. Substantially immobilizing the one or more materials may be performed as described further herein. For example, substantially immobilizing the one or more materials in an imaging volume of a measurement device may include applying a magnetic field to one side of an imaging chamber that defines the imaging volume of the measurement device. In addition, this method may include any other step(s) described herein. Furthermore, this method may be performed by any of the systems described herein.

The system embodiments described herein configured to transfer one or more materials and/or to image one or more materials may or may not be configured to substantially immobilize the one or more materials according to embodiments described herein. For example, immobilization of the particles in the imaging volume may also be performed using magnetic attraction as described above, a vacuum filter substrate, or any other appropriate method known in the art. Examples of methods and systems for positioning microspheres for imaging are illustrated in U.S. patent application Ser. No. 11/270,786 to Pempsell filed Nov. 9, 2005, which is incorporated by reference as if fully set forth herein. Regardless of the particle immobilization method, the particles are preferably substantially immobilized such that the particles do not move perceptibly during the detector integration period, which may be multiple seconds long.

Two or more of the system embodiments described herein can be combined into a single embodiment such that the single embodiment provides all of the advantages of the two or more system embodiments. For example, a further embodiment relates to a system configured to transfer one or more materials to an imaging volume of a measurement device from one or more storage vessels, to image the one or more materials in the imaging volume, to substantially immobilize the one or more materials in the imaging volume, or some combination thereof. The system may be configured to transfer the one or more materials as described herein, to image the one or more materials as described herein, to substantially immobilize the one or more materials as described herein, or some combination thereof. This system may be further configured as described herein.

Accordingly, another embodiment relates to a method for transferring one or more materials to an imaging volume of a measurement device from one or more storage vessels, imaging the one or more materials in the imaging volume, substantially immobilizing the one or more materials in the imaging volume, or some combination thereof. Transferring, imaging, and substantially immobilizing the one or more materials may be performed as described further herein. In addition, this method may include any other step(s) described herein. Furthermore, this method may be performed by any of the systems described herein.

The measurements described herein generally include image processing for analyzing one or more images of particles to determine one or more characteristics of the particles such as numerical values representing the magnitude of fluorescence emission of the particles at multiple detection wavelengths. Subsequent processing of the one or more characteristics of the particles such as using one or more of the numerical values to determine a token ID representing the multiplex subset to which the particles belong and/or a reporter value representing a presence and/or a quantity of analyte bound to the surface of the particles can be performed according to the methods described in U.S. Pat. No. 5,736,330 to Fulton, U.S. Pat. No. 5,981,180 to Chandler et al., U.S. Pat. No. 6,449,562 to Chandler et al., U.S. Pat. No. 6,524,793 to Chandler et al., U.S. Pat. No. 6,592,822 to Chandler, and U.S. Pat. No. 6,939,720 to Chandler et al., which are incorporated by reference as if fully set forth herein. In one example, techniques described in U.S. Pat. No. 5,981,180 to Chandler et al. may be used with the fluorescent measurements described herein in a multiplexing scheme in which the particles are classified into subsets for analysis of multiple analytes in a single sample.

It will be appreciated to those skilled in the art having the benefit of this disclosure that this invention is believed to provide systems and methods for performing measurements of one or more materials. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system for performing a bioassay where one or more analytes are exposed to a plurality of magnetically responsive particles to form a sample, comprising:
    a sample container for holding a sample;
    an imaging chamber, where:
        the imaging chamber has a first interior surface and a second interior surface and the first interior surface is opposite the second interior surface; and
        the imaging chamber is configured for receiving a portion of the sample comprising a plurality of magnetically responsive particles;
    a sample valve coupled to the sample container, a reservoir, and the imaging chamber, where the sample valve is capable of being placed in a first position that creates a fluid connection between the sample container and the reservoir and a second position that creates a fluid connection between the reservoir and the imaging chamber;
    a pump configured to convey the sample from the sample container to the reservoir and from the reservoir to the imaging chamber;
    a magnet outside the imaging chamber and configured to be selectively positioned proximate to the first interior surface of the imaging chamber such that the plurality of magnetically responsive particles are substantially dispersed in a monolayer on the first interior surface of the imaging chamber;
    an illumination source outside the imaging chamber and positioned to provide light that passes through the second interior surface of the imaging chamber before reaching the first interior surface of the imaging chamber;
    a photosensitive detector outside the imaging chamber and configured to detect light exiting the imaging chamber through the second interior surface; and
    a processor programmed to:
        cause the sample valve to be placed in the first position;
        cause the pump to convey, using suction, the sample from the sample container through the sample valve and into the reservoir;
        cause the sample valve to be placed in the second position;
        cause the pump to convey the sample from the reservoir to the imaging chamber;
        cause the magnet to move from a first position to a second position, where the second position is closer to the first interior surface of the imaging chamber than the first position;
        cause the illumination source to illuminate the sample;
        cause the photosensitive detector to detect light emitted from the sample;
        cause the magnet to move from the second position to the first position; and
        cause the pump to convey the sample out of the imaging chamber.

2. The system of claim 1, wherein the illumination source comprises a plurality of LED's arranged in a ring.

3. The system of claim 2, wherein the photosensitive detector is arranged substantially perpendicular to the first interior surface of the imaging chamber and substantially central to the ring.

4. The system of claim 2, wherein the photosensitive detector is arranged substantially parallel to the first interior surface of the imaging chamber.

5. The system of claim 2, wherein the illumination source and the photosensitive detector each comprise one or more lenses and filters.

6. The system of claim 1, comprising a fluid chamber for holding washing fluid and where the processor is further programmed to cause washing fluid to flow through the imaging chamber while the magnet is in the second position.

7. The system of claim 1, wherein the first internal surface of the imaging chamber comprises a pattern of recesses.

8. The system of claim 7, wherein the plurality of recesses comprise a one-dimensional (1D) or two-dimensional (2D) pattern of recesses.

9. The system of claim 7, wherein the pattern of recesses comprises a pattern of square recesses.

10. The system of claim 7, wherein the pattern of recesses comprises a pattern of triangular recesses.

11. The system of claim 1, further comprising one or more additional magnets configured to be selectively positioned proximate to the first interior surface of the imaging chamber.

12. The system of claim 1, wherein the illumination source comprises an illumination module including one or more LEDs, wherein for each LED, the illumination module further comprises:
    a filter interposed between a respective LED and the imaging chamber;
    a lens system comprising two normal refractive lenses interposed between the respective LED and the filter for collecting light from the respective LED and pseudo-collimating the collected light through the filter; and
    another lens interposed between the filter and the imaging chamber to focus light transmitted through the filter onto the imaging chamber.

13. The system of claim 1, where the illumination source is positioned circumferentially around the first interior surface of the imaging chamber.

14. The system of claim 1, further comprising:
    a pump valve coupled to the pump and the reservoir, where the pump valve is capable of being placed in a first position that creates a fluid connection between the pump and the reservoir and a second position that creates a fluid connection between the pump and a drive solution container; and
    where the processor is further programmed to:
        cause the pump valve to be placed in the first position before causing the pump to convey, using suction, the sample from the sample container through the sample valve and into the reservoir;
        cause the pump valve to be placed in the second position to allow a drive solution in the drive solution container to enter the pump; and
        cause the pump valve to be placed in the first position to allow the pump to convey drive solution into the reservoir.

* * * * *